United States Patent [19]

Moss et al.

[11] Patent Number: 5,514,600
[45] Date of Patent: May 7, 1996

[54] MAMMALIAN GUANINE NUCLEOTIDE BINDING PROTEIN WITH AN ADP-RYBOSYLATION FACTOR DOMAIN

[75] Inventors: Joel Moss, Bethesda; Koichi Mishima, Rockville; Maria S. Nightingale, Bethesda, all of Md.; Mikako Tsuchiya, Izumo, Japan

[73] Assignee: The United States of America as represented by the Department of Health and Human Services, NATIONAL INSTITUES OF HEALTH, Bethesda, MD

[21] Appl. No.: 312,648

[22] Filed: Sep. 27, 1994

Related U.S. Application Data

[60] Division of Ser. No. 49,473, Apr. 19, 1993, Pat. No. 5,386,021, which is a continuation-in-part of Ser. No. 49,252, Apr. 16, 1993, abandoned.

[51] Int. Cl.$^6$ ............... G01N 33/543; C08L 89/00; C12P 21/02; C12N 15/12
[52] U.S. Cl. ............... 436/518; 435/7.1; 435/7.21; 435/7.23; 435/7.92; 530/350; 530/828; 530/815
[58] Field of Search ............... 530/350, 388.21, 530/815, 828; 435/7.1, 7.21, 7.92, 975, 7.23, 69.1, 71.1, 72.3, 320.1; 436/518

[56] References Cited

PUBLICATIONS

Bobak, et al. "Molecular cloning, characterization, and expression of human ADP–ribosylation factors: Two guanine nucleotide–dependent activators of cholera toxin" *Proc. Natl. Acad. Sci.* USA 86: pp. 6101–6105 (1989).
Boman, et al. "A role for ADP–ribosylation factor in nuclear vesicle dynamics" *Nature* 358: pp. 512–514 (1992).
Kahn, et al. "The Amino Terminus of ADP–ribosylation Factor (ARF) Is a Critical Determinant of AFR Activities and Is a Potent and Specific Inhibitor of Protein Transport" *J. Biol. Chem.* 267: 18 pp. 13039–13046 (1992).
Kahn, et al. "Human ADP–Ribosylation Factors" *J. Biol. Chem.* 266:4 pp. 2606–2614 (1992).
Lee, et al., "Characterization of the Human Gene Encoding ADP–ribosylation Factor 1, a Guanine Nucleotide–binding Activator of Cholera Toxin" *J. Biol. Chem.* 267:13 pp. 9208–9034 (1990).
Monaco, et al. Abstract: "Identification of a New Form of ADP–ribosylation Factor by Polymerase Chain Reaction" *Proc. Natl. Acad. Sci* USA 87: pp. 2206–2210 (1990).
Monaco, et al. "Selective amplification of an mRNA and related pseudogene for a human ADP–ribosylation factor, a guanine nucleotide–dependent protein activator of cholera toxin" *Proc. Natl. Acad. Sci.* USA 87: pp. 2206–2210 (1990).
Murtagh, et al. "Guanine Nucleotide–binding Proteins in the Intestinal Parasite *Giardia lamblia*" *J. Biolog. Chem.* 267:14 pp. 9654–9662 (1992).
Price, et al. "Effects of Phospholipid and GTP on Recombinant ADP–ribosylation Factors (ARFs)" *J. Biolog. Chem.* 267:25 pp. 17766–17772 (1992).
Price, et al. "Guanine nucleotide–binding proteins that enhance choleragen ADP–ribosyltransferase activity: Nucleotide and deduced amino acid sequence of an DP–ribosylation factor cDNA" *Proc. Natl. Acad. Sci.* USA 85: pp. 5488–5491 (1988).
Serafini, et al. "ADP–ribosylation Factor is a Subunit of the Coat of Golgi–derived COP–coated Vesicles: A Novel Role for a GTP–binding Protein" *Cell* 67: pp. 239–253 (1991).
Sewell, et al. "Sequences of the Bovine and yeast ADP–ribosylation factor and comparison to other GTP–binding proteins" *proc. natl. Acad. Sci.* USA 85: pp. 4620–4624 (1988).
Stearns, et al. "ADP–ribosylation factor is functionally and physically associated with the Golgi complex" *Proc. Natl. Acad. Sci.* USA 87: pp. 1238–1242 (1990).
Tsai, et al. "Isolation and Characterization of the Human Gene for ADP–ribosylation Factor 3, a 20–kDa Guanine Nucleotide–binding Protein Activator of Cholera Toxin" *J. Biol. Chem.* 266:34 pp. 23053–23059 (1991).
Tsai, et al. "Stimulation of Choleragen Enzymatic Activities by GTP and Two Soluble Proteins Purified from Bovine Brain" *J. Biol. Chem.* 263:4 1768–1772 (1988).
Tsuchiya, et al., "Molecular Identification of ADP–Ribosylation Factor mRNAs and Their Expression in Mammalian Cells" *J. Biolog. Chem.* 266:5 pp. 2772–2777 (1991).
Tsuchiya, et al. "Tissue and Species Distribution of mRNA Encoding Two ADP–ribosylation Factors, 20–kDa Guanine Nucleotide Binding Proteins" *Biochemistry* 28: pp. 9668–9673 (1989).

*Primary Examiner*—Mary E. Mosher
*Assistant Examiner*—Laurie Scheiner
*Attorney, Agent, or Firm*—Knobbe, Martens, Olson & Bear

[57] ABSTRACT

The invention provides a method for detecting the presence of ARD 1 protein in a sample. The method includes the steps of providing labeled or immobilized anti-ARD 1 antibody in a reaction zone, introducing sample into the reaction zone such that ARD 1 protein in the sample, if present, will react with said antibody to form an immunological complex, and detecting the formation of said immunological complex. Cells, nucleotide and amino acid sequences and vectors associated with ARD 1 are also described.

3 Claims, 7 Drawing Sheets

```
                       10         20         30         40         50         60         70
SEQ.ID NO:27 hARF1   1 MGNIFANLFK GLFGKKEMRI LMVGLDAAGK TTILYKLKLG EIVTTIPTIG FNVETVEYKN ISFTVWDVGG
SEQ.ID NO:28 bARF2   1 ****V*EK*** S********* ********** ********** ********** ********** **********
SEQ.ID NO:29 hARF3   1 *****G**L* S*I******* ********** ********** ********** ********** **********
SEQ.ID NO:30 hARF4   1 LTISSS R***Q* ******** ****** ****** ******** *C********
SEQ.ID NO:31 hARF5   1 LTVSAS RI**Q* ******** ****** ****** ******** *C********
SEQ.ID NO:32 hARF6   1 KVLSK--- --IFN* L***** ****** QS*V *****T* VK*N******
SEQ.ID NO:33 hARD1 403 *--------  ------*I*V VTL*G* ***F*QD *FMQP*** ****** LKI*****

80         90        100        110        120        130        140
hARF1   71 QDKIRPLWRH YFQNTQGLIF VVDSNDRERV NEAREELMRM LAEDELRDAV LLVFANKQDL PNAMNAAEIT
bARF2   71 ********** ********** ********** *****T**** ********** *****V**** **********
hARF3   71 ******** ****** ********I Q*VAD**QK* ******** L***** **AIS*M*
hARF4   71 R***K* ******** ********I Q*SAD**QK* *Q****** ****M **PVS*L*
hARF5   71 ********** *YTG**** *CA**D*I D*QH*I INDR*M***I I*I******* *DKPHQ
hARF6   67 ********** *YL***AVV* ****SH*D*I SHSAKL *T*K***L I******V AG*LSVE***
hARD1  457 KH*L*****K* ********** ********** ********** ********** ********** **********

150        160        170        180
hARF1  141 DKLGLHSL-R HRNWYIQATC ATSGDGLYEG LDWL-SNQLR NQK      181
bARF2  141 ********-* Q********* ********** ****-****K ***      181
hARF3  141 ********-* N*TV ****** -A****K *K*     181
hARF4  141 *****Q**-* **Q*T***** **Q*T***** ****-**E*S KR       180
hARF5  141 ****QH*-* S*TV Q*T***D* ****-*HE*S KR        180
hARF6  135 E****TRI-* D****V*PS* ********** *TT*YKS          175
hARD1  528 EL*S***K*CC G*S****GCD *RM* **-*RQ*V AAGDLDVA  574
```

FIG.1

MAMMALIAN GUANINE NUCLEOTIDE BINDING PROTEIN WITH AN ADP-RYBOSYLATION FACTOR DOMAIN

This is a divisional of U.S. application Ser. No. 08/049,473, filed Apr. 19, 1993 now U.S. Pat. No. 5,386,021 which is a continuation-in-part of the parent application, U.S. application Ser. No. 08/049,252, filed Apr. 16, 1993, now abandoned.

BACKGROUND

Monomeric guanine nucleotide-binding proteins of the ras superfamily of 18–30 kDa function in a variety of cellular processes including signaling, growth, immunity, and protein transport (Barbacid, H. *Annu. Rev. Biochem.* 56: 779–828 (1987); Bourne, H. R. *Cell* 53:669–671 (1988); Bourne, et al. *Nature* (London) 349:117–127 (1991); Gabig, et al. *J. Biol. Chem.* 262: 1685–1690 (1987); Goud, et al. *Nature* (London) 345:553–556 (1990); Hall, A. *Science* 249:635–640 (1990); Knaus, et al. *Science* 254: 1512–1515 (1991)). ADP-ribosylation factors (ARFs) constitute one family of the ras superfamily.

ARF was initially identified as a factor required for cholera toxdin-catalyzed ADP-ribosylation of $G_{sa}$, the stimulatory guanine nucleotide-binding (G) protein of the adenylylcyclase system (Kahn, et al. *J. Biol. Chem.* 259: 6228–6234 (1984); Serventi, et al. *In: Current Topics in Microbiology and Immunology* 175, (Aktories, K. ed) pp. 43–67, Springer-Verlag, Berlin Heidelberg (1992). In the presence of GTP or a nonhydrolyzable GTP analogue, ARF serves as an allosteric activator of cholera toxin ADP-ribosyltransferase (Noda, et al. *Biochim. Biophys. Acta* 1034: 195–199 (1990); Tsai, et al. *J. Biol. Chem.* 263: 1768–1772 (1988); Tsai, et al. *Proc. Natl. Acad. Sci.* (*USA*) 84: 5139–5142 (1987)). It stimulates the toxin-catalyzed ADP-ribosylation of proteins unrelated to $G_{sa}$ and simple guanidino compounds such as arginine and agmatine as well as auto-ADP-ribosylation of the toxin A1 protein (Noda, et al. *Biochim. Biophys.* Acta 1034: 195–199 (1990); Tsai, et al. *J. Biol. Chem.* 263:1768–1772 (1988); Tsai, et al. *Proc. Natl. Acad. Sci.* (*USA*) 84:5139–5142 (1987)).

ARFs are evolutionarily well conserved and present in all eukaryotes from Giardia to mammals (Kahn, et al. *J. Biol. Chem.* 263:8282–8287 (1988); Murtagh, et al. *J. Biol. Chem.* 267:9654–9662 (1992); Tsai, et al. *J. Biol. Chem.* 266: 8213–8219 (1991); Tsuchiya, et al. *Biochemistry* 28: 9668–9673 (1989); Tsuchiya, et al. *J. Biol. Chem.* 266: 2772–2777 (1991)). Immunologically, they have been localized to the Golgi apparatus of several types of cells (Stearns et al. *Proc. Natl. Acad. Sci.* (*USA*) 87:1238–1242 (1990)). ARFs are required for association of nonclathrin coat proteins with intracellular transport vesicles (Serafini, et al. *Cell* 67: 239–253 (1991)) and also appear to be critical during an early step in endocytosis as well as in nuclear vesicle fusion (Boman, et al. *Nature* (London) 358: 512–514 (1992); Lenhard, et al. *J. Biol. Chem.* 267:13047–13052 (1992)). GTP binding and hydrolysis may be involved in binding of ARF to membranes, and the nonhydrolyzable GTP analogue $GTP_\gamma S$, but not GTP or GDP, promotes the association of cytosolic ARF with Golgi (Regazzi, et al. *Biochem. J.* 275:639–644 (1991)) 1991) or phospholipid membranes (Kahn, et al. *J. Biol. Chem.* 266:15595–15597 (1991); Walker, et al. *J. Biol. Chem.* 267: 3230–3235 (1992)).

By molecular cloning from cDNA and genomic libraries, and PCR amplification of RNA transcripts, six mammalian ARFs, two yeast ARFs, and two Giardia ARFs have been identified (Bobak, et al. *Proc. Natl. Acad. Sci.* (*USA*) 86: 6101–6105 (1989); Monaco, et al. *Proc. Natl. Acad. Sci.* (*USA*) 87: 2206–2210 (1990); Murtagh, et al. *J. Biol. Chem.* 267:9654–9662 (1992); Price, et al. *Proc. Natl. Acad. Sci.* (*USA*) 85: 5488–5491 (1988); Sewell, et al. *Proc. Natl. Acad. Sci.* (*USA*) 85: 4620–4624 (1988); Stearns, et al. *Mol. Cell. Biol.* 10: 6690–6699 (1990); Tsuchiya, et al. *J. Biol. Chem.* 266:2772–2777 (1991)). Mammalian ARFs fall into three classes based on deduced amino acid sequences, gene structure, phylogenetic analysis, and size (Lee, et al. *J. Biol. Chem.* 267:9028–9034 (1992); Tsuchiya, et al. *J. Biol. Chem.* 266: 2772–2777 (1991)). Class I ARFs are ARFs 1–3; class II includes ARFs 4 and 5; and class III has ARFs 6. Some lipids and/or detergents, e.g., SDS, cardiolipin, dimyristoylphosphatidylcholine (DMPC)/cholate, enhance ARF activities (Bobak, et al. *Biochemistry* 29:855–861 (1990); Noda, et al. *Biochim. Biophys. Acta* 1034: 195–199 (1990); Tsai, et al. *J. Biol. Chem.* 263:1768–1772 (1988)). Members of the ARF multigene family, when expressed as recombinant proteins in *E. coli*, display different phospholipid and detergent requirements (Price, et al. *J. Biol. Chem.* 267: 17766–17772 (1992)). Following synthesis in *E. coli* all of these ARFs had enhanced cholera toxin ADP-ribosyltransferase activity in the presence of GTP' (Kahn, et al. *J. Biol. Chem.* 266: 2606–2614 (1991); Price, et al. *J. Biol. Chem.* 267: 17766–17772 (1992); Weiss, et al. *J. Biol. Chem.* 264: 21066–21072 (1989)).

In general, differences in the various ARF sequences are concentrated in the amino-terminal regions and the carboxyl portions of the proteins. Only three of 17 amino acids includin Met[1] and Gly[2], in the amino termini are identical among ARFs, and four amino acids in this region of ARFs 1–5 are missing in ARF 6 (Tsuchiya, et al. *J. Biol. Chem.* 266: 2772–2777 (1991)). It was recently reported (Kahn, et al. *J. Biol. Chem.* 267:13039–13046 (1992)) that the amino-terminal regions of ARF proteins form an α-helix, and that this domain is required for membrane targeting, interaction with lipid, and ARF activity.

Schliefer et al., (*J. Biol. Chem.* 257: 20–23 (1991)) described a protein distinctly larger than ARF that possessed ARF-like activity. At the time of those studies however, it had not been demonstrated that ARF requires GTP for activity, so functional characterization of the protein did not include assessment of that property.

SUMMARY

The present invention relates to a novel 64 kDa protein styled ARD 1. This protein includes an 18 kDa region that exhibits significant homology to known ADP-ribosylation factors (ARFs), but lacks a 15 amino acid domain previously thought necessary for ARF stimulation. The remaining 46 kDa sequence is apparently unlike any known protein. Both rat and human sequences are specifically disclosed.

One aspect of the present invention, therefore, comprises a polynucleotide encoding ARD 1 (which substantially has the sequence of SEQ ID NO:1 or which otherwise substantially encodes the sequence of SEQ ID NO:2) in isolated or purified form. An isolated polynucleotide is one that has been largely separated from other nucleotides, so that the polynucleotide in any composition of which it is a part is at least 1%, preferably 5% or 10%, and more preferably at least about 20%, 30%, or 50% the particular polynucleotide of interest. Mammalian ARD 1 sequences are of particular interest, and vertebrate sequences such as rat and human sequences are particularly preferred.

The present invention also includes a recombinant DNA sequence in the form of a nucleic acid expression vector, comprising the DNA of SEQ ID NO:1 operably linked to a promoter. The promoter may be a heterologous promoter, for example, and is preferably adapted to direct expression of the polynucleotide in a host cell.

The present invention also includes a cell transfected with the expression vector discussed above. Such a cell is preferably capable of expressing ARD 1 protein. Secretion sequences of the type well known in the art may be included in the expression vector that are adapted to promote secretion of the protein in the cell in question. Although the transfected cell may be procaryotic, it is preferably a eukaryotic cell line. CHO cells, for example, are suitable for use in the present invention. Other mammalian cell lines, including human cell lines, may be used, as well other vertebrate cell lines. Alternatively, insect cell lines may be used for expressing the protein of the present invention.

One preferred embodiment of the present invention is an ARD 1 protein composition, comprising the polypeptide of SEQ ID NO:2 in a concentration of at least about 0.01 µg/g. The composition of Claim 3, wherein the polypeptide is in substantially purified form.

Also disclosed is an immunoassay kit, comprising ARD 1 protein as a polypeptide reagent, a reaction unit including a reaction zone in which the polypeptide reagent can interact with antibodies (if any) in the sample directed against ARD 1 to forman immunological complex, and means for detecting the reaction or lack of reaction of the polypeptide with the antibodies. Similarly, the present invention includes an immunoassay kit where anti-ARD 1 antibodies are used as a reagent to react with ARD 1 (if any) in a sample, and the reaction of the antibody and ARD 1 are detected.

Another aspect of the present invention relates to isolated or purified antibody against ARD 1 protein. Both polyclonal antibody and monoclonal antibody against ARD 1 protein are contemplated. Moreover, the monoclonal antibody of the present invention is not necessarily isolated or purified.

A further aspect of the present invention is a method for detecting the presence of ARD 1 protein in a sample, comprising the steps of providing labeled or immobilized anti-ARD 1 antibody in a reaction zone, introducing sample into the reaction zone such that ARD 1 protein in the sample, if present, will react with the antibody to form an immunological complex, and detecting the formation of the immunological complex.

BRIEF DESCRIPTION OF THE FIGURES

FIG. 1 is a table showing a comparison of amino acid sequences of ARD 1 and mammalian ARFs. The deduced amino acid sequence of reported human and bovine ARFs and the ARF domain of human ARD 1 were aligned using PC/Gene CLUSTAL. hARF 1, human ARF (Bobak, et al. *Proc. Natl. Acad. Sci.* (*USA*) 86:6101–6105 (1989)); bARF 2, bovine ARF 2 (Price, et al. *Proc. Natl. Acad. Sci.* (*USA*) 85:5488–5491 (1988); hARF 3, human ARF 3 ((Bobak, et al. *Proc. Natl. Acad. Sci.* (*USA*) 86: 6101–6105 (1989)); hARF 4 human ARF 4 (Monaco, et al. *Proc. Natl. Acad. Sci.* (*USA*) 87:2206–2210 (1990)); hARF 5 and hARF 6, human ARF 5 and human ARF 6, respectively (Tsuchiya, et al. *J. Biol. Chem.* 266:2772–2777 (1991)); hARD 1, the ARF domain of human ARD 1. Gap penalty and window size were both 10. Asterisks and hyphens indicate amino acids identical to hARF 1 and gaps, respectively.

DETAILED DESCRIPTION

Figure 2:
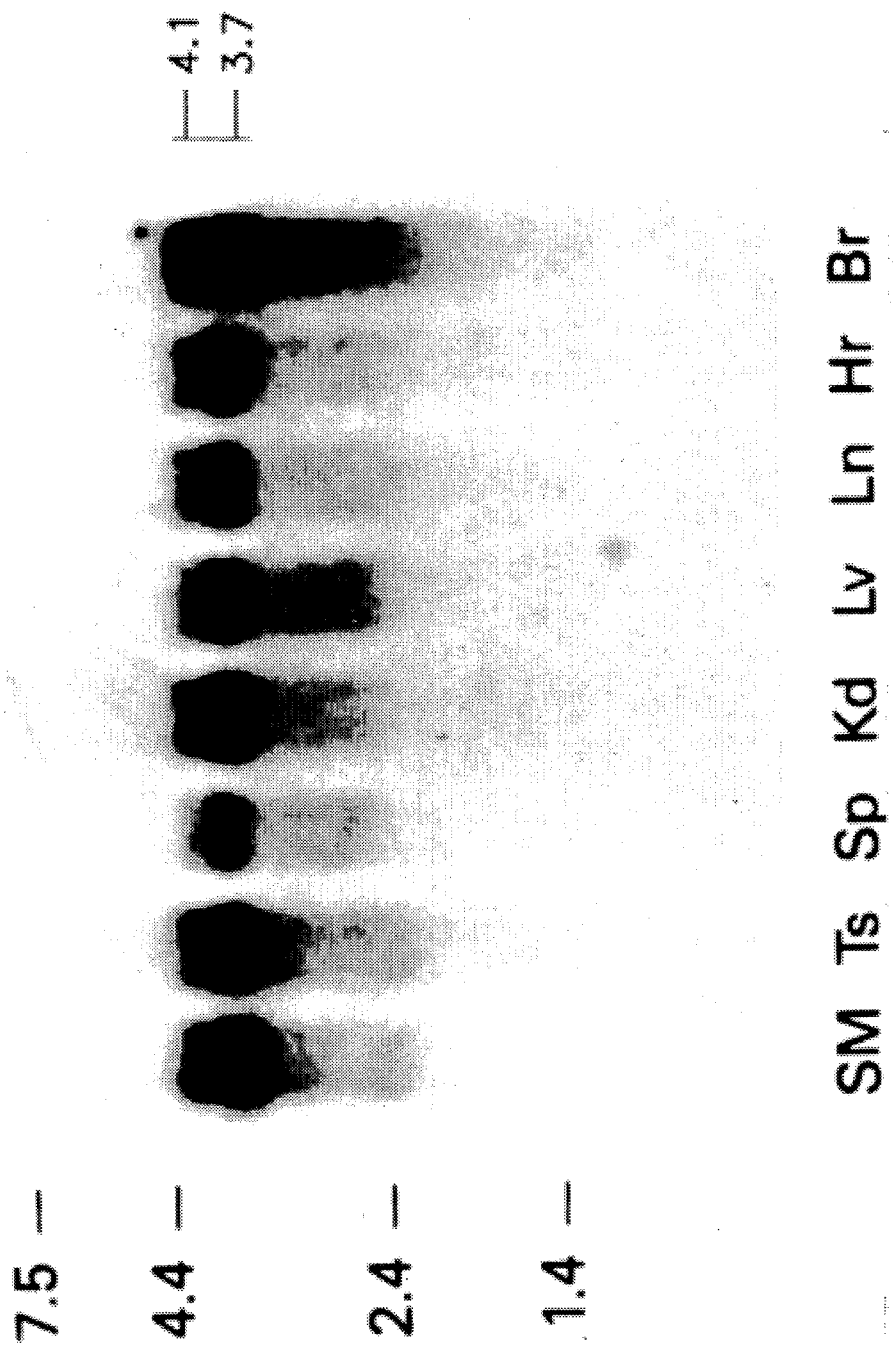
FIG. 2 is a copy of a Northern blot showing the hybridization of poly(A)+ RNA from rat tissues with ARD 1 coding region cDNA. Poly(A)+ RNA from rat skeletal muscle (SM), testis (Ts), spleen (Sp), kidney (Kd), liver (Lv), lung (Ln), heart (Hr) and brain (Br) was hybridized with human ARD 1 coding region cDNA. Positions (kb) of standards (left and ARD 1 mRNA (3.7, 4.1, right) are indicated.

The present invention includes the discovery of a newly recognized member of the ADP-ribosylation factor (ARF) super family termed ARD 1. We have isolated the polynucleotide encoding ARD 1 from both human and rat libraries, as described below. In addition, ARD 1 has been transfected into a host cell and expressed. Upon expression, a 64-kDa guanine nucleotide-binding protein containing an 18-kDa, functional ARF domain at its carboxy terminus termed ARD 1 (for ARF domain) was found.

Recombinant human ARD 1, and a recombinant truncated species containing only the ARF domain following expression, activated cholera toxin ADP-ribosyltransferase in a GTP-dependent manner, consistent with the conclusion that 15 amino acids adjacent to the amino terminus of ARF proteins fare not required for toxin activation.

The ARD 1 protein of the present invention is useful for stimulation of cholera toxin ADP-ribosyltransferase. Thus, as a reagent for synthetic biochemistry, it can stimulate toxin-catalyzed ribosylation of such molecules as agmatine in a GTP-dependent manner. It can also be used as a reagent in diagnosis of ADP-ribosylation deficiency disease. ARD 1 includes a GTP binding region, and may be used for binding GTP. It is also useful for generation of anti-ARD 1 antibodies, and as a reagent in assays for ARD 1 and for antibodies against ARD 1. Moreover, ARD 1 is a member of the ARF superfamily, and may be used in general in the same way as known ARF proteins.

ARD 1, a new member of the ARF family, was identified by molecular cloning from cDNA libraries and by Rapid Amplification of cDNA Ends (RACE) type PCR. Nucleotide and amino acid sequences of human and rat ARD 1 are, respectively, 92% and 96% identical. In all rat tissues tested, 3.7-kb and 4.1-kbARD 1 mRNAs were detected. A cDNA probe specific for the ARD 1 coding region hybridized with poly(A)$^+$ RNA of similar sizes from rat, mouse and rabbit brains, and human cultured cells. The specific probe additionally hybridized to a somewhat different size mRNA from chicken brain. Sequence and hybridization data are thus consistent with the conclusion that these ARF-related proteins are highly conserved in eukaryotic cells.

The unique 64-kDa ARD 1 protein is much larger than other monomeric guanine nucleotide-binding proteins and consists of two distinct domains. One domain is a carboxy-terminal ARF domain and the remainder, doesn't have homology with other known ARF domains. In fact, the sequence of the non-ARF domain has no homology to any sequences in the GenBank data base and contains no motif known to be conserved in any guanine nucleotide-binding proteins.

These conserved motifs, denoted $GX_1X_2X_3X_4GK$, $DX_1X_2G$, and NKXD using the single letter amino acid code, are conserved in other GTP-binding proteins including heterotrimeric G proteins, and ras, rho, and rab proteins. Unlike rab, ras, rho, and $G_\alpha$, ARF and ARD 1 have an Aspartic Acid (D) at position $X_2$ in $GX_1X_2X_3X_4GK$. Like $G_\alpha$, but unlike the ras super family, $X_1$ and $X_2$ in the $DX_1X_2G$ sequence of ARD 1 and ARFs are Valine (V) and Glycine (G), respectively. The ARF domain contains several motifs common to all ARFs, such as GLDGAGK, DVGG, and NKQD, which are considered to be responsible for GTP-binding (see FIG. 1). The CAT sequence is, however, represented by DAR. The conserved alanine, based on homology to ras, is thought to be involved in guanine nucleotide-binding. In fact, a recombinant protein, representing the ARF domain of ARD 1 had the ability to bind GTP, while the entire ARD 1 protein, under the same conditions did not bind GTP. The reason is unclear, although it is possible that when bound to a nitrocellulose membrane, the conformation of the larger protein limits accessibility of GTP to the binding site.

It has been suggested that the amino terminus of ARF is critical for its function, since mutant ARF 1 protein lacking the amino-terminal 17 amino acids was unable to stimulate cholera toxin-catalyzed ADP-ribosylation of $G_{S\alpha}$ in the presence of DMPC/cholate, although it still possessed GTP$_\gamma$S binding activity that no longer required DMPC/cholate (Kahn, et al. *J. Biol. Chem.* 267:13039–13046 (1992)). Similarly, ARD 1 fusion protein or its ARF domain fusion protein did not have demonstrable ARF activity in the presence of SDS, DMPC/cholate or cardiolipin, all of which are effective in supporting activity of ARFs (Noda, et al. *Biochim. Biophys. Acta* 1034: 195–199 (1990); Serventi, et al. *In: Current Topics in Microbiology and Immunology* 175, (Aktories, K. ed) pp. 43–67, Springer-Verlag, Berlin Heidelberg (1992); Tsai, et al. *Proc. Natl. Acad. Sci. (USA)* 84:5139–5142 (1987)).

In the presence of Tween 20, however, ARD 1 protein stimulated toxin-catalyzed ADP-ribosylation of agmatine in a GTP-dependent manner. Removal of the non-ARF domain from ARD 1 protein significantly diminished its ARF activity and increased the GTP concentration required for half maximal activity, suggesting some role for the non-ARF domain in its ARF-like activity. Clearly, however, these data are consistent with the notion that toxin activation does not require the amino-terminal 15 amino acids of ARF, although they may contribute to interaction with phospholipids.

As a first step, we isolated cDNA from a human HL-60 lambda library that had homology with known ARF sequences. Materials:

[$\alpha$-$^{32}$P]dATP (6,000 Ci/mmol), [$\alpha$-thio$^{35}$S]dATP (1,350 Ci/mmol), and [$\alpha$-$^{32}$P]GTP (800 Ci/mmol) were purchased from DuPont-New England Nuclear; [adenine-$^{14}$C]NAD (273 Ci/mol) from Amersham (Arlington Heights, Ill.); random-primed DNA labeling kit and GDP$\beta$S from Boshringer Mannheim (Indianapolis, Ind.); human fetal brain cDNA and rat brain cDNA Lambda ZAP library from Stratagens (La Jolla, Calif.); competent *E. coli* DH5$\alpha$ (maximal efficiency), terminal deoxynucleotidyl transferase and pSPORT 1 from Life Technology (Gaithersburg, Md.); plasmid purification kit from Qiagen (Chatsworth, Calif.); DNA sequencing kit from United States Biochemical Corp. (Cleveland, Ohio); AMV reverse transcriptass, NotI, SalI, RNase inhibitor (RNasin) and T4 DNA ligase from Promega (Madison, Wis.); Centricon 100 from Amicon (Danvers, Mass.); nylon membrane (Nytran) and nitrocellulose membrane from Schleicher and Schuell (Keens, N.H.); Thermus aquaticus DNA polymerase from Perkin-Elmer/Cetus (Norwalk, Conn.); glutathione, glutathione-agarose, cardiolipin, DMPC, cholate, and NAD from Sigma (St. Louis, Mo.); and AG1-$X_2$ from Bio-Rad (Richmond, Calif.). Oligonucleotides were synthesized using an Applied Biosystems 380B DNA synthesizer.

Experiment 1: Analysis of ARD 1 cDNA

A cyclic, AMP-differentiated HL-60 Lambda ZAP library ($5\times10^5$ plaques) was screened by plaque hybridization with ARF 2B cDNA (Price, et al. *Proc. Natl. Acad. Sci. (USA)* 85: 5488–5491 (1988)) and a mixture of oligonucleotides denoted XARFC as described by Tsuchiya et al., (*J. Biol. Chem.* 266: 2772–2777 (1991)). The only clone (#76) that was positive with the ARF 2B cDNA and negative with oligonucleotides specific for ARFs 1–6 (Tsuchiya et al., *J. Biol. Chem.* 266:2772–2777 (1991)) was plaque-purified, the insert was excised in vivo by the method of Short et al.(*Nucleic Acids Res.* 16: 7583–7600 (1988)). The insert was then purified using Qiagen, and sequenced by the Sanger et al. method (*Proc. Natl. Acad. Sci. (USA)* 74: 5463–5467 (1977)). The 1660-bp insert (nucleotides 706–2365 in Table I) included an open reading frame (1207–1722) encoding an ARF domain of 172 amino acids.

TABLE I

Nucleotide and Protein Alignment of Human and Rat ARD 1

```
                                                                                           -22 CTGTGGGCGCTTCCCCTGCGAGG
HUMAN (SEQ ID NO:2)           1     M  A  T  L  V  V  N  K  L  G      A  G  V  D  S  G  R  Q  G  S      R  G  T  A  V  V  K  V  L  E
HUMAN (SEQ ID NO:1)           1    ATGGCTACCCTGGTTGTAAACAAGCTCGGA    GCGGGAGTAGACAGTGGCCGGCAGGGCAGC    CGGGGACAGCTGTAGTGAAGGTGCTAGAG
RAT                                 --------------------------       ----------------------------      ------------G-------G-------

HUMAN                        31     C  G  V  C  E  D  V  F  S  L      Q  G  D  K  V  P  R  L  L  L      C  G  H  T  V  C  H  D  C  L
HUMAN                        91    TGTGGAGTTTGTGAAGATGTCTTTCTTTG    CAAGGAGACAAAGTTCCCGTCTTTTGCTT    TGTGGCCATACCGTCTGTCATGACTGTCTC
RAT                                 --------T--------------------    ------------T-----C-----C---     -----------------C--A--------

HUMAN                        61     T  R  L  P  L  H  G  R  A  I      R  C  P  F  D  R  Q  V  T  D      L  G  D  S  G  V  W  G  L  K
HUMAN                       181    ACTCGCCTACCTCTCATGGAAGAGAGCAATC   CGTTGCCCATTTGATGACAAGTAACAGAC    CTAGGTGATTCAGGTGTCTGGGATTGAAA
RAT                                 T-----T--G------------------A     -------------G--------------     ------------------A---------

HUMAN                        91     K  N  F  A  L  L  E  L  L  E      R  L  Q  N  G  P  I  G  Q  Y      G  A  A  E  E  S  I  G  I  S
HUMAN                       271    AAAAATTTTGCTTTATTGGAGCTTTTGGAA    CGACTTCAGAATGGGCCTATTGGTCAGTAT    GGAGCTGCAGAAGAATCATTGGGATATCT
RAT                                 --------------C--------------     --TT----A------A-A-----------     --------------G-C------------

HUMAN                       121     G  E  S  I  R  C  D  E  D         E  A  H  L  A  S  V  Y  C  T      V  C  A  T  H  L  C  S  E  C
HUMAN                       361    GGAGAGAGCATCATTCGTTGTGATGAAGAT    GAAGCTCACCTTGCCTCTGTATATTGCACT    GTGTGTGCAACTCATTTGTGCTCTGAGTGT
RAT                                 -------------T-----C---------     ----------G--A----G-C---------    -------------G--------A------

HUMAN                       151     S  Q  V  T  H  S  T  K  T  L      A  K  H  R  R  V  P  L  A  D      K  P  H  E  K  T  M  C  S  Q
HUMAN                       451    TCTCAAGTTACTCATTCTACAAAGACATTA    GCAAAGCACAGGCGAGTTCCTCTAGCTGAT    AAACCTCATGAGAAAACTATGTGCTCTCAG
RAT                                 -----------------------A------    --C-------T--------G----------    -------------G-C-------G

HUMAN                       181     H  Q  V  H  A  I  E  F  V  C      L  E  E  G  C  Q  T  S  P  L      M  C  C  V  C  K  E  Y  G  K
HUMAN                       541    CACCAGGTGCATGCCATTGAGTTTGTTGTC    TTGGAAGAAGGTTGTCAAACTAGCCCACTC    ATGTGCTGTGTCTGCAAAGAATATGGAAAA
RAT                                 --------------A---------------    ----C--------T--------T----T-     ------------------C-----------

HUMAN                       211     H  Q  G  H  K  H  S  V  L  E      P  E  A  N  Q  I  R  A  S  I      L  D  M  A  H  C  I  R  T  F
HUMAN                       631    CACCAGGGTCACAAGCATTCAGTATTGGAA    CCAGAAGCTAATCAGATCCGAGCATCAATT    TTAGATATGGCTCACTGCATACGACCTTC
RAT                                 --------------------C-----C--G    --------------C-----G---------    -----------------C--A--------

HUMAN                       241     T  E  E  I  S  D  Y  S  R  K      L  V  G  I  V  Q  H  I  E  G      G  E  Q  I  V  E  D  G  I  G
HUMAN                       721    ACAGAGGAAATCTCAGATTATTCCAGAAAA    TTAGTTGGAATTGTGCAGCACATTGAAGGA    GGAGAACAAATCGTGGAAGATGGAATTGGA
RAT                                 ----T--G--------------------      ---------------G------T------     -------------------A---------

HUMAN                       231     M  A  H  T  E  H  V  P  G  T      A  E  N  A  R  S  C  I  R  A      Y  F  Y  D  L  H  E  T  L  C
HUMAN                       811    ATGGCTCACACAGAACATGTACCAGGGACT    GCAGAGAATGCCGGTCATGTATTCGAGCT    TATTTTTATGATCTACATGAAACTCTGTGT
RAT                                 ------------G------C-----T---     ------A--A-----A-------G-CA--     ----------------------C--T-G-

HUMAN                       301     R  Q  E  E  M  A  L  S  V  V      D  A  H  V  R  E  K  L  I  W      L  R  Q  Q  E  D  M  T  I
HUMAN                       901    CGTCAAGAAGAAATGGCTCTAAGTGTTGTT    GATGCTCATGTTCGTGAAAAATTGATTTGG    CTCAGGCAGCAACAAGAAGATATGACTATT
RAT                                 ----------------C-------G-----    ------------------C-----------    ----T------------------G-----

HUMAN                       331     L  L  S  E  V  S  A  A  C  L      H  C  E  K  T  L  Q  Q  D  D      C  R  V  V  L  A  K  Q  E  I
HUMAN                       991    TTGTTGTCAGAGGTTTCTGCAGCCTGCCTC    CACTGTGAAAAGACTTTGCAGCAGGATGAT    TGTAGAGTTGTCTTGGCAAAACAGGAAATT
RAT                                 C-C-------CC-----AA--------T--    --T---------------------------    -----------------------A-----C
```

TABLE I-continued

Nucleotide and Protein Alignment of Human and Rat ARD 1

```
HUMAN  361   T R L L T E L Q K Q         Q Q Q F T E V A D H         I Q L D A S I P V T
HUMAN        ACAAGGTTACTGGAAACATTGCAGAAACAG  CAGCAGCAGTTTACAGAAGTGCAGATCAC  ATTCAGTTGGATGCCAGCATCCCTGTACT
RAT    1081  ----- A--- T- A-----------      ---------------------------    ----------- T- T- A-----------

HUMAN  391   F T K D N R V H I G         P K M E I R   V V T L       G L D G A G K T T I
HUMAN        TTTACAAAGGATAATCGAGTTCACATTGGA  CCAAAAATGGAAATTCGGGGTCGTTACGTTA GGATTGGATGGTGCTGGAAAAACTACTATC
RAT    1171  ---------------- C- CA---- T- T---  - C--------- A- A- A- C- A---     ----------- A---------------- T

HUMAN  421   L F K L K Q D E F M         Q P I P T I G F N V         E T V E Y K N L K F
HUMAN        TTGTTTAAGTTAAAACAGGATGAATTCATG  CAGCCCATTCCAACAATTGGTTTTAACGTG GAAACTGTAGAATATAAAAATCTAAAATTC
RAT    1261  --------------- C--------- A---- ------------- T--------------    --------- G-------- C---------

HUMAN  451   T I W D V G G K H K         L R P L W K H Y Y L         N T Q A V V F V V D
HUMAN        ACTATTTGGGATGTAGGTGGAAAACACAAA  TTAAGACCATTGTGGAAACATTATTACCTC AATACTCAAGCTGTTGTGTTTGTTGTAGAT
RAT    1351  - C-------- G--- A------------   ---------------------------    ---------- A---------- T- C----

HUMAN  481   S S H R D R I S E A         H S E L A K L L T E         K E L R D A L L L I
HUMAN        AGCAGTCATAGAGACAGAATTAGTGAAGCA  CACACGGAACTGCAAAGTTGTTAACGGAA  AAAGAACTCCGAGATGCCCTGCTCCTGATT
RAT    1441  ----- C-----------------------  --------------- G-------- A--- ------- T-- A- T-----------

HUMAN  511   F A N K Q D V A G A         L S V E E I T E L L         S L H K L C C G R S
HUMAN        TTTGCTAACAAACAGGATGTTGCTGGAGCA  CTGTCAGTAGAAGAAATCACTGAACTACTC AGTCTCCATAAATTATGCTGTGGCCGTAGC
RAT    1531  ---------------------- C----- G --- T- G- T----------- C---- T--  ------------------ C- AA- G----

HUMAN  541   W Y I Q G C D A R S         G M G L Y E G L D W         L S R Q L V A A G V
HUMAN        TGGTATATTCAGGGCTGTGATGCTCGAAGT  GGTATGGGACTGTATGAAGGGTTGGACTGG CTCTCACGGCAACTTGTAGCTGCTGGAGTA
RAT    1621  ---------------------- A-----  -------------- G- C- C--------  - G- C------------ G---- C---- G

HUMAN  571   L D V *
HUMAN        TTGGATGTTGCTTGATTTTAAAGGCAGCAG  TTGTTTGAAGTTTGTGTGGTTAAAGTAACT TTGCACATAAAAAAAAAAAAAAAAATGCA
HUMAN  1711  TCTCAAAAGATGGTAATTTAGGATGCATAT  ATATATATATATATATAAAGGAATTCTTGGA TTGGGAATTCAGTACTTCTTTGCTTTAAAAAA
       1801  TTTTGTGGCAGAATTATTTCTAATTGAC    GCAGATTAGATTGAATTAAATAGAAACTTA  TTGAATATACATTCTTTTAAAAGTATATT
       1891  TGTTATTTAAGTTTTCAGATAATATGTGA   CCAATTACTGGGAAAGAGTAGTCACAGA    GAAAGGGTAAGTGAAGTGTTATTCTTTCAG
       1981  TGAAAAAAGAATAGCCAATTGAGTGCCTAA  TGAGACCTCTGTGTGAAGCAAGTGAAGTAT AGCTGCTTCTTTTAACCTGCCTTTTCACTG
       2071  AATGTTGCAGCATTAGTAGTAGAAATGA    CAGTTGCTTAATGAAATAGAATCCAAACTA  CATATTTGGATAATAGGATTACTTTATGTT
       2161  TATGTTCAGAGTTAACAGAACACCTTTAAT GCTAAGAACTATAAGGTACAGAAAATTAAT  ACTTTATATAGTGTTTTATTAACTTCTCC
       2251  TACAGCATTTTGTATAAACACAATGAGGG   AGTGAAATTGTACCCAATTAGGCTGTCAG   AGCTCTAAATTGGTCCTCTCATTTTTCAAC
       2341  GTGGAAGTAATTGGATCTGAATTTATGAAA  GACCCATTTCCAGGACTGAACCTAGGTCAG  GTAAAATGTAGTAAGTAAGCAGAACCAGG
       2431  AAATTTAAAGTAATATTTCTTTCTAATATA  ATATTGCATCCTTTGTGGGAATGACTATAG GTACAGTGGCAAATGCTTATTACTTACTTC
       2521  GTTGGCTTATTTAAAAGCTAGTGACCTAA   ATAGAAAGCGAACTTCAAGAGAAGTTGTAA  AAGGCCTTGAAATGTACTCTAGAGGAAAA
       2611  AAACTGTTTCCCAAAATAAGTGCATTATT   TTACAATAATTATTCAGTGTTGTGAGTAAA  TAAAAATGTGTCTCTTTACTGTTTTTCAT
       2701  ATGTCTAAAGAAAAAAATTCAAAAAGT     TTATTTAAAGATTATTCAGTGTTTTT      TTTTAAATGTTCTGATACATTAGGATGAAGT
       2791  TTTTAAAGAATATTATTATGGACACGAT    GTAAGGACAGTGATGTCTGGTAACAAGATG  TGACTTTTGGTAGCACTGTGTGGTTCAT
       2881  TAAATCTAAATCTTATTAGTTGAATTGTT   GTACAAGTTTAGAAAACAAAGCATTAAAAA  AAAAGCCTATCAGTTATTATGGCAATATG
       2971  TCTTTTCAAATCTATTTTGTTTAAAACA    ATTTTCAGGTAAAAGGTCATGCTGTTACA   GGTGTAGTTTGTGTGCATAAATAATACTTC
       3061  TAAATAAATAATTGTAATTTCATCCTTT
       3151  CGAATTAATTATTTAATATTTGACTGATT                                  ATTGCTCTGTGAG
```

Table I illustrates the Nucleotide and deduced amino acid sequences of human and rat ARD 1 cDNA. The human ARD 1 deduced amino acid sequence is shown in single-letter code above the nucleotide sequence on the respective codon of the human ARD 1 coding region. Differences in rat ARD 1 nucleotide sequences are shown below the human sequence. The rat ARD 1 sequence is available from positions corresponding to 61 to 1726 of human ARD 1. The human nucleotide sequence shown is SEQ ID NO:1, the rat nucleotide sequence shown is SEQ ID NO:3 and the translated human amino acid sequence shown is SEQ ID NO:2.

An oligonucleotide specific for this sequence (J1R) is shown in Table II and was used to screen a human fetal brain cDNA Lambda ZAP library ($5 \times 10^5$ plaques). Among eight positive clones, #7-3 contained nucleotides 7–1826 and clone #7-8 contained nucleotides 726–3225. In this sequence, about 1200 nucleotides preceded the ARF region without a stop codon in the same reading frame.

400 ng of primer JK723RII (Table II) in 10 mMTris-HCl, pH 8.3, 50 mM KCl, 1.5 mM $MgCl_2$, 0.01% gelatin, dNTP, 200 µM each, 0.1% Tween, Taq DNA polymerase, 2.5 units (total volume, 100 µl).

TE (1 ml) was added to the PCR products and the mixture was concentrated (Centricon 100). TE (2 ml) was added followed by concentration to 30 µl and transfer of a sample (1 µl) to a second PCR amplification (40 cycles: 95° C., 30 seconds; 50° C., 30 seconds; 72° C., 30 seconds) with 400 ng each of primers SALAD (Table III) and JKNOT (Table II). Preparations were digested with NotI and SalI, ligated into plasmid pSPORT1, and used to transform competent DH5α cells, which were then grown on LB/agar plates containing ampicillin, 100 µg/ml.

TABLE II

Oligonucleotides used in the analysis of ARD 1

| Name | Sequence 5' - 3' | |
|---|---|---|
| J1R | AATGGGCTGCATGAATTCATCCTGTTTTAA | (SEQ ID NO:3) |
| | complementary to bases 1270 to 1299 of human ARD 1. | |
| JK721RC | CCTCCTTCAATGTGCTGCACAATTCC | (SEQ ID NO:4) |
| | complementary to bases 757 to 782 of human ARD 1. | |
| JK723RII | TGAGTAACTTGAGAACACTC | (SEQ ID NO:5) |
| | complementary to bases 445 to 464 of human ARD 1. | |
| JK728R | TGCCCTGCCGGCCACTGTCTACTCCCGCTCCGAGCTTGTTTA | (SEQ ID NO:6) |
| | complementary to bases 17 to 58 of human ARD 1. | |
| JKNOT | GACTAGTTCTAGATCGCGAGCGGCCGCCCTTCACCTAGGTCTGTTACTTGTCG | (SEQ ID NO:7) |
| | complementary to bases 226 to 248 of human ARD 1 with 30 bases added at 5' end to introduce NotI site. | |
| JK8EX | GGCCTGGTTCCGCGGATGGCTACCCTGGTTGTA | (SEQ ID NO:8) |
| | bases 1 to 18 of human ARD 1 with 15 bases added at 5' end to introduce ligation-independent cloning site. | |
| JK3EX | GGCCTGGTTCCGCGGATGGAAATTCGGGTC | (SEQ ID NO:9) |
| | bases 1207 to 1221 of human ARD 1 with 15 bases added at 5' end to introduce ligation-independent cloning site. | |
| JKEXR | CTGCGCCTCGCTCCTCAAGCAACATCCAA | (SEQ ID NO:10) |
| | complementary to bases 1711 to 1725 of human ARD 1 with 14 bases added at 5' end to introduce ligation-independent cloning site. | |
| JK5EXR | CTGCGCCTCGCTCCTTTTGGTCCAATGTG | (SEQ ID NO:11) |
| | complementary to bases 1192 to 1206 of human ARD 1 with 14 bases added at 5' end to introduce ligation-independent cloning site. | |

To further characterize the 5'-terminus of this cDNA, 5'-RACE was carried with the poly(A)$^+$ RNA from IMR-32 human neuroblastoma cells.

EXPERIMENT 2: 5'-RACE with IMR-32 Poly (A)$^+$ RNA:

Poly(A)$^+$ RNA (5 µg) from IMR-32 human neuroblastoma cells was reverse-transcribed with the primer JK721RC, as shown in Table II (100 ng) by AMV reverse transcriptass (20 units) in 50 mM Tris-HCl, pH 8.3, 7 mM $MgCl_2$, 40 mM KCl, 1 mM dithiothreitol, dNTPs (1 mM each), bovine serum albumin (0.1 mg/ml), RNasin, 20 units (total volume 20 µl) at 42° C. for 3 hours. TE (10 mM Tris-HCl, pH 7.5, 1 mM EDTA), 1 ml, was added and the mixture was concentrated (Centricon 100). After addition of 2 ml of 0.2×TE, it was concentrated again to 50 µl.

The reverse transcribed products (46 µl) were tailed with terminal deoxynucleotidyl transferase (30 units) at 37° C. for 5 minutes in 0.1M potassium cacodylate, pH 7.2, 2 mM $CaCl_2$, 0.2 mM dithiothreitol, 0.2 mM dATP followed by heat inactivation of the enzyme (65° C., 5 min) The preparation (20 µl) was subjected to PCR (40 cycles: 95° C., 30 seconds; 50° C., 30 seconds; 72° C., 60 seconds) with 200 ng each of primers SALAD and SALADTT (Table III) and

TABLE III

Oligonucleotides used in the analysis of ARD 1

| Name | Sequence, 5' - 3' |
|---|---|
| RA4CF | ATGGGCCTCACCAT<br>(SEQ ID NO:12)<br>Bases 1 to 14 of rat ARF 4. |
| HARF4-codAR | TCTCACTGATGGCCATAGCA<br>(SEQ ID NO:13)<br>Complementary to bases 396 to 415 of rat and human ARF 4 cDNA. |
| HRA4CR | TCATTTGACAGCCA<br>(SEQ ID NO:14)<br>Complementary to bases 514 to 527 of rat and human ARF 4 cDNA. |
| REKNOT | GACTAGTTCTAGATCGCGAGCGGCCGCCCTGGATATCTAACCAAGGACAT<br>(SEQ ID NO:34)<br>Bases 552 to 571 of rat ARP 4 with 40 bases added at 5'-end to introduce a NotI site. |
| RDK1CF | TTGATAGAATTGGTCTAGGCTTGTTACAAC<br>(SEQ ID NO:15)<br>Bases 574 to 603 of rat ARF 4 cDNA (just after stop codon). |
| RDK1R | GTTGTAACAAGCCTAGACCAATTCTATCAA<br>(SEQ ID NO:16)<br>Complementary to RDK1CF |
| RDK3R | GGCTAAACAGCAACATTGTTCTTGGTAAACAATAATTGGCAACAAAAC<br>(SEQ ID NO:17)<br>Complementary to bases 677 to 724 of rat ARF 4 cDNA (after first polyadenylation signal). |
| RDK4R | TCAGTGAGTTCCAAGGGGGTAACTTTAAAACATTATTGGTGTGGGCTC<br>(SEQ ID NO:18)<br>Complementary to bases 855 to 902 of rat ARF 4 CDNA (after second polyadenylation signal). |
| RAKRIIa | TGGAATCGGAACTTCCAGATCCTCATCGTCOGAGTCCGATTCACTCTG<br>(SEQ ID NO:19)<br>Complementary to bases 127 to 174 of rat RIIα cDNA (regulatory subunit of cAMP-dependent protein kinase) (30). |
| SALADTT | CTCGTGGACGATGTTGCTGTCGACCCACGCGTCCG(T)20<br>(SEQ ID NO:20)<br>Oligo(dT) with 35 bases containing a SalI site at 5'-end. |
| SALAD | CTCGTGGACGATGTTGCTGTCGACCCACGCGTCCG<br>(SEQ ID NO:21) |
| R2SCR | TTTGTACKAGATCGTCGTTTTGCCAGCTGCATCTAAGCC<br>(SEQ ID NO:22)<br>Used for screening. |
| RDK5NOT | GACTAGTTCTAGATCGCGAGCGGCCGCCACCACCGCTATCGGC<br>(SEQ ID NO:23)<br>Bases -12 to 6 with 25 bases added to introduce a NotI site. |
| RDKSAL1 | CTCGTGGACGATGTGCTGGTOGACAGCTGCCCAAACCGTCTCAG<br>(SEQ ID NO:24)<br>Complementary to bases 638 to 655 with 26 bases added at 5'-end to introduce SalI and PuuII sites. |
| RDKSAL2 | CTCGTGGACGATGTGCTGGTCGACGTTAACACTCAAAACAGATTT<br>(SEQ ID NO:25)<br>Complementary to bases 833 to 850 with 27 bases added at 5'-end to introduce SalI and PuuII sites. |
| RDKSAL3 | CTCGTGGACGATGTGCTGGTCGACTCGAAAAATCATTTTATTAGGAATAATTCCA<br>(SEQ ID NO:26)<br>Complementary to bases 1362 to 1389 with 27 bases added at 5'-end to introduce SalI and TagI sites. |

Following transfection of the reverse transcribed, PCR amplified sequences into competent DH5α cells, we isolated clones corresponding to ARD 1.

EXPERIMENT 3: Isolation of ARD 1 from Human and Rat

Colonies were screened with probe JK728R (Table II) that had been labeled with [α-$^{32}$P]dATP and terminal deoxynucleotidyl transferase. Positive clones (33) were selected and grown in LB containing ampicillin, 100 μg/ml. Plasmid DNA was purified and digested with Sal I and Not I. Longer inserts (~350 bp) from seven clones were sequenced. A consensus sequence of the 5'-terminal sequences of four are shown in Table I; three clones had shorter inserts.

Four clones with the longest inserts had an initiation codon ATG accompanied by A at −3 and G at position 4. This sequence is believed favorable for translation initiation (Kozak, et al. *J. Cell. Biol.* 108:229–241 (1989)). The putative open reading frame of this gene, termed ARD 1, consisted of 1722 nucleotides encoding a protein of 574 amino acids with an ARF related domain at the carboxyl terminus. We anticipated that human and rat ARD 1 were likely similar, so we isolated clones corresponding to rat ARD 1.

A rat brain Lambda ZAP II library (6×10$^5$ plaques) was screened with an oligonucleotide R2SCR (TABLE III) that yielded clone 2$^a$ containing an insert that corresponded to nucleotides 61–1973 of human ARD 1. A comparison of the rat and human sequences is provided in Table I.

Nucleotide and deduced amino acid sequences of ARD 1 coding regions from rat and human are 92% and 98% identical, respectively, without any gaps. The nucleotide sequence of the ARF domain of human ARD 1 is 60–66% identical to those of the mammalian ARFs; the deduced amino acid sequences are 55–60% identical or 69–72% similar including conservative placements (Table IV).

TABLE IV

Comparison of nucleotide and deduced amino acid sequences of the ARF domain of human ARD 1 (172 amino acids) to those of mammalian ARFs

| Mammalian ARF | Percentage identity to hARD 1 | |
|---|---|---|
| | Nucleotides | Amino acids |
| hARF 1 | 62 | 59 (71)* |
| bARF 2 | 66 | 59 (72) |
| hARF 3 | 65 | 60 (72) |
| hARF 4 | 66 | 59 (72) |
| hARF 5 | 62 | 56 (72) |
| hARF 6 | 60 | 55 (69) |

*identical plus conservative replacements Programs used were PC/Gene FASTSCAN for nucleotide sequence and PC/Gene PALIGN (open gap cost, 1; unit gap cost, 1) for amino acid sequence.

Some of the regions common to ARFs thus far identified that are believed to be involved in guanine nucleotide binding and TP hydrolysis are also conserved in ARD 1 (FIG. 1), i.e., GLDGAGK (411–417), DVGG (454–457), and NKQD (513–516); CAT, however, is missing and replaced with DAR (547–549).

To analyze the expression of ARD 1, we probed Northern blots of RNA from various tissues.

EXPERIMENT 4: Northern Analysis of ARD 1:

Poly(A)+ RNA was isolated from total RNA (Chomyc-zynski, et al. *Anal. Biochem.* 162:156–159 (1987)) using oligo(dT) chromatography (Chirgwin, et al. *Biochemistry* 18: 5294–5299 (1979)). Poly(A)+ RNA (5 µg) was then fractionated by electrophoresis in 1.2% agarose/formaldehyde gels and transferred to Nytran.

Prehybridization and hybridization were carried out at 42° C. in hybridizaton buffer of 5×SSC (1×=0.15M NaCl, 0.015M sodium citrate, pH 7.0), 5×Denhardt's solution (1×=0.02% Ficoll, 0.02% polyvinylpyrrolidone, 0.02% bovine serum albumin), 10 mM Tris-HCl, pH 7.4, 0.1% SDS, 10% dextran sulfate, denatured salmon sperm DNA, 0.1 mg/ml, 40% formamide. Filters were washed at 55° C. once with 2×SSC, 0.5% SDS and twice with 0.5×SSC, 0.5% SDS. Filters were exposed to Kodak XAR film at −80° C. with an intensifying screen. Human ARF 1 coding region cDNA was prepared as described by Bobak et al. (*Proc. Natl. Acad. Sci. (USA)* 86: 6101–6105 (1989)). Human ARD 1 coding region cDNA was generated by PCR as described above.

Figure 3:
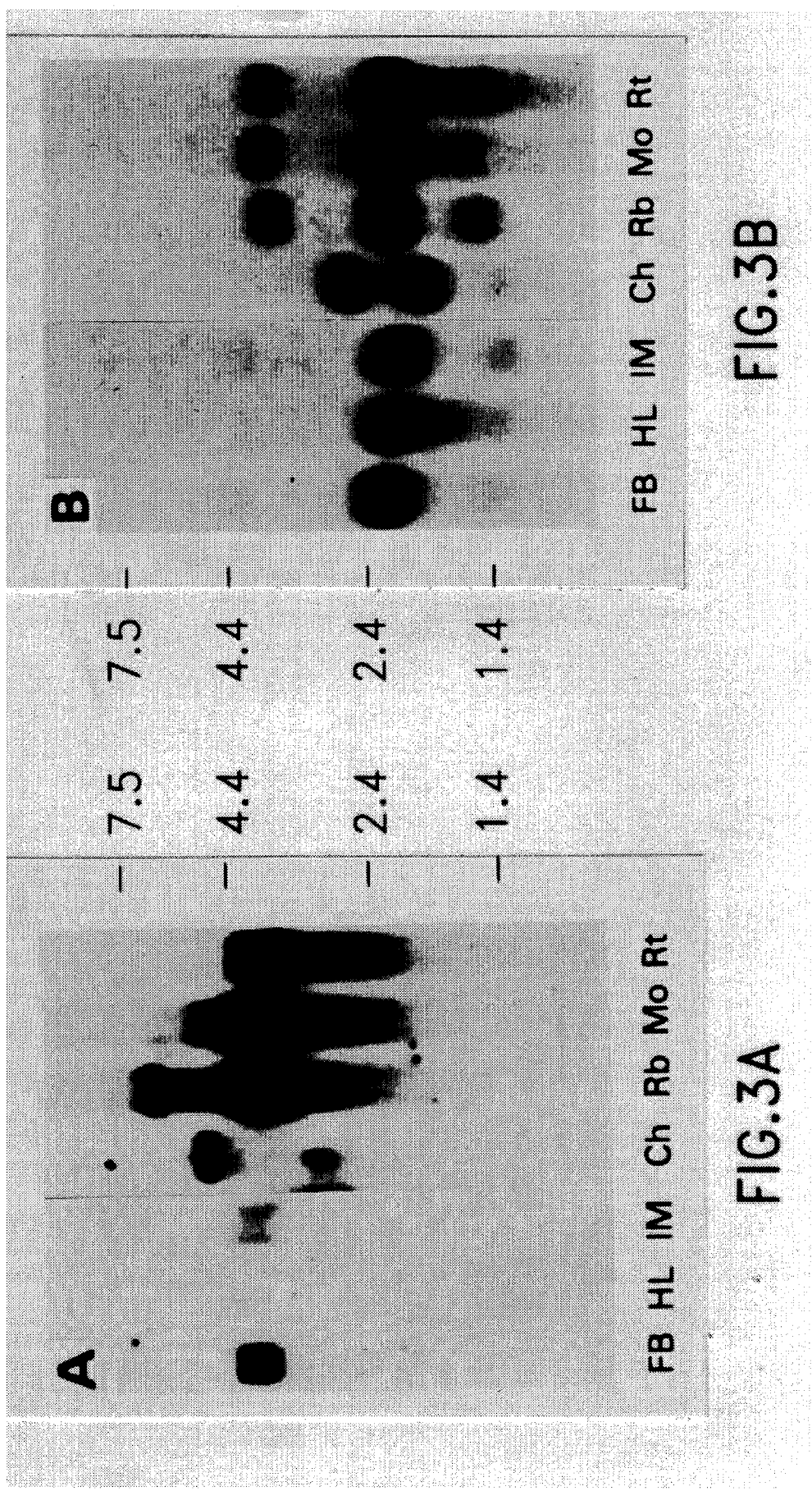
FIG. 3 is a copy of a Northern blot illustrating the hybridization of poly (A)+ RNA from different species with ARD 1 coding region cDNA. Poly (A) + RNA from human fibroblasts (FB), HL-60 (HL), and IMR-32 (IM) cells and brain from chicken (Ch), rabbit (Rb), mouse (Mo), and rat (Rt) was hybridized with human ARD 1 coding region cDNA FIG. 3A or human ARF 1 coding region cDNA FIG. 3B as described below. Positions of standards (kb) are indicated.

An ARD 1 coding region cDNA clone hybridized with 4.2-kb and 3.7-kb mRNAs from all rat tissues examined (FIG. 2). This probe also hybridized with bands of similar size in poly(A)+ RNA from mouse and rabbit brain and human fibroblasts. Poly(A)+ RNA from IMR-32 cells, however, hybridized very weakly while RNA from undifferentiated HL-60 cells did not hybridize detectably. However, all samples of poly(A)+ RNA hybridized essentially equally well with a human ARF 1 coding region cDNA (FIG. 3).

To assess the ability of ARD 1 to enhance cholera toxin ADP-ribosyltransferase, recombinant GST-ARD 1 fusion proteins were prepared.

EXPERIMENT 5: Expression of the Fusion Proteins:

Three ARD 1 fusion proteins with glutathione S-transferase (GST) were synthesized employing a ligation-independent cloning method (Haun et al. Gene 112: 39–43 (1992)), using clone #7–3 and oligonucleotide primers as indicated in Table II. For GST-p8 (containing the entire sequence from Met$^1$ to Ala$^{574}$), oligonucleotides JK8EX and JKEXR (Table II) were used. For GST-p3 (the ARF domain from Met$^{403}$ to Ala$^{574}$), oligonucleotides JK3EX and JKEXR (Table II) were used. For GST-p5 (the non-ARF sequence from Met$^1$ to LYs$^{402}$) oligonucleotides JK8EX and JK5EXR (Table II) were used. The fusion proteins were purified with glutathione-agarose by well known methods as described in Smith et al. (*Gene* 67: 31–40 (1988)). To test the ability of each fusion protien to bind GTP we performed the following experiments.

EXPERIMENT 6: GTP-binding Assay with Recombinant ARD1

Fragment p3 (2 µg), p8 (4 µg), and sARF II (0.2 µg) were subjected to electrophoresis in 4–20% polyacrylamide gels with SDS and transferred to nitrocellulose. The membrane was incubated in 50 mM Tris-HCl, pH 7.5, 150 mM NAcl, 2 mM dithiothreitol, 2.5 mM EDTA, soybean trypsin inhibitor, 10 µg/ml, 0.5 mM PMSF, 0.3% bovine serum albumin, 0.#% Tween 20 (binding buffer) at room temperature for 2 h, transferred to fresh binding buffer containing 8 mM $MgCl_2$ and [$\alpha$-$^{32}P$]GTP (800 Ci/mmol), 1 µCi/ml, for 2 h, washed three times with binding buffer for 5 min, briefly dried, and exposed to Kodak XAR film at −80° C. overnight with intensifying screen.

The affinity of GST-p3 for GTP was apparently lower than that of GST-p8, p8 or sARF II. GTP concentrations required for half-maximal activation were less than 10 µM with GST-p8, p8, and sARF II and ~50 µM with GST-p3.

Figure 4:
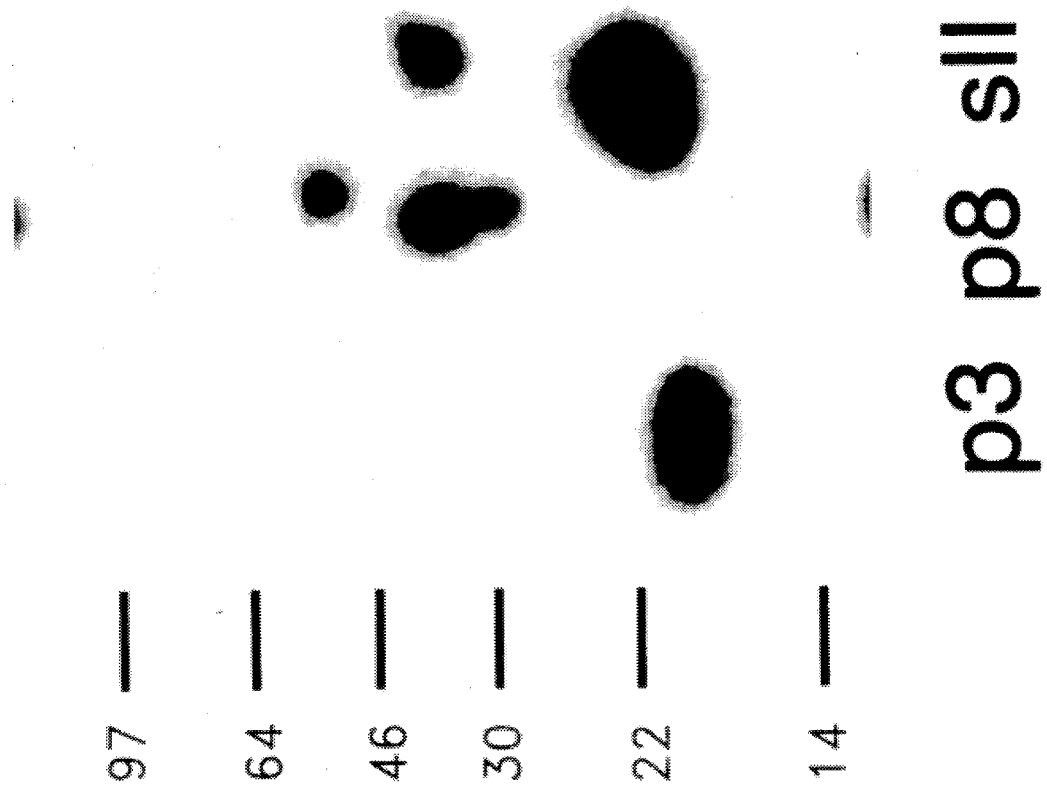
FIG. 4 is copy of a protein gel illustrating the binding of GTP to recombinant ARD 1. p3 (2 µg), p8 (Mg) and sARF II (0.2 µg) were subjected to 4–20% SDS-polyacrylamide gel electrophoresis, and transferred to nitrocellulose membrane. [α-$^{32}$P]GTP binding was carried out in the presence of 0.3% Tween 20 as described below.

Through the use of specific primers, as discussed above, GST-p8 contained the entire ARD 1 protein, GST-p3 contained the carboxy-terminal ARF domain, and GST-p5 contained the non-ARF domain. The recombinant ARF domain of ARD 1 bound GTP after SDS-PAGE and transfer to nitrocellulose membrane, whereas P8, which contained the entire sequence of ARD 1, exhibited no detectable binding (FIG. 4). It is possible that the longer p8 protein was unable to bind GTP due to a conformational change when attached to the nitrocellulose membrane. The shorter GST-p3 protein, however, was able to bind GTP even after attachment to the nitrocellulose membrane.

Figure 5:
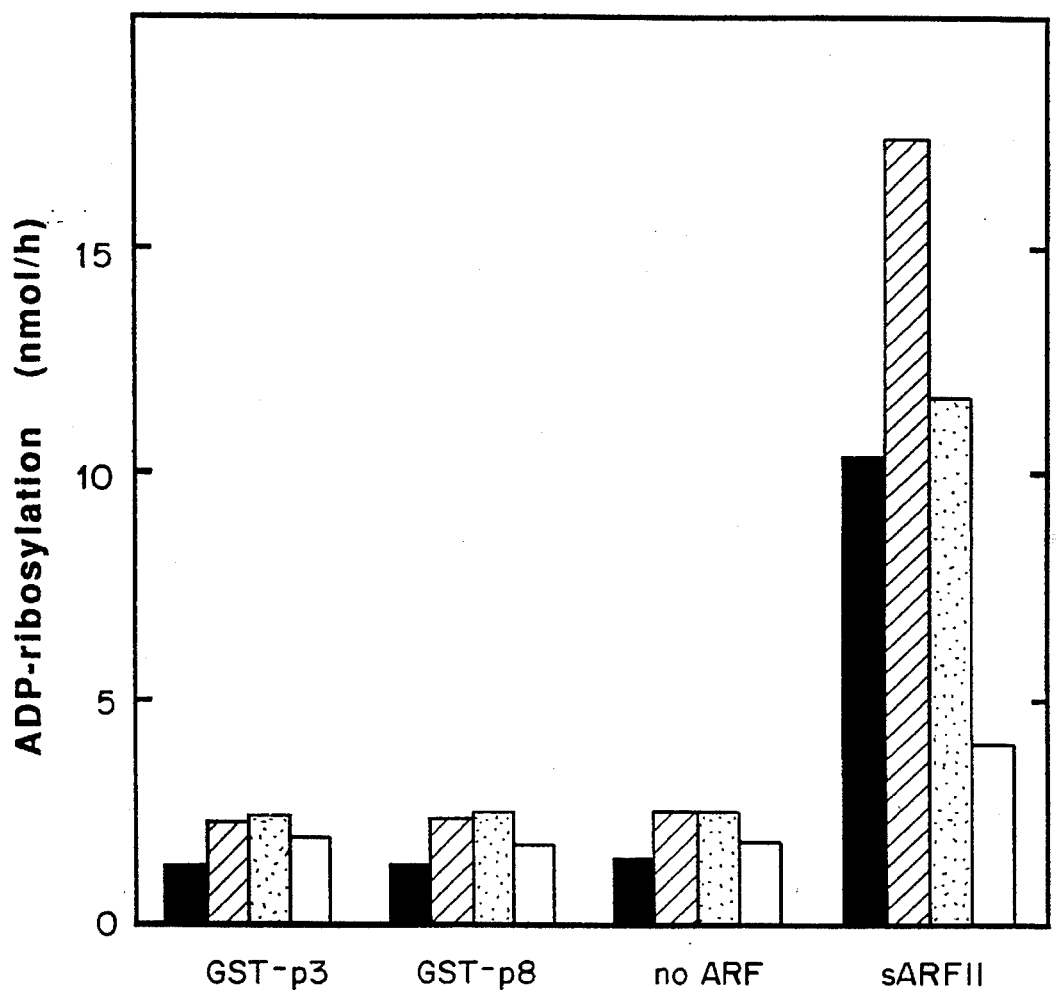
FIG. 5 is a bar graph illustrating the effects of lipids/detergents on ARF activity. Cholera toxin-catalyzed ADP-ribosylation of agmatine was assayed in the presence of GST-p3 (4 µg), GST-p8 (8 µg), sARF II (2 µg) or no ARF as described below. The lipids/detergents used were 0.003% SDS (■), 1 mg/ml cardiolipin (striped rectangles), 3 mMDMPC/0.4% cholate (dotted rectangles) or 0.4% cholate (hollow rectangles).

As shown in FIG. 5, ARD 1 fusion proteins did not stimulate ADP-ribosylation by cholera toxin in the presence of SDS, DMPC/cholate, or cardiolipin, which to differing degrees enhanced the activity of sARF II. In the presence of 0.3% Tween 20, however, recombinant ARD 1, P8, and GST-p8 increased the toxin ADP-ribosyltransferase in a dose-dependent manner (FIG. 6).

EXPERIMENT 7: NAD/Agmatine ADP-ribosylation Assay:

Stimulation of cholera toxin-catalyzed ADP-ribosylation of agmatine was assayed to evaluate ARF activity of the recombinant proteins. Reaction mixtures contained 50 mM potassium phosphate (pH 7.5), 4 mM $MgCl_2$, 30 mM dithiothreitol, ovalbumin (0.3 mg/ml), 0.2 mM [adenine-$^{14}C$]NAD (o.05 µCi), 20 µM agmatine, 0.3% Tween 20, cholera toxin (0.5 µg), 1 mM GTP or 0.1 mM GDPβS, and the indicated amount of sARF II or recombinant protein (total volume 200 µl). After incubation at 30° C. for 1 hour, duplicate samples (80 µl) were transferred to columns of AG1-$X_2$ equilibrated with water and eluted five times with five 1 ml washes of water. The eluate, containing [$^{14}C$]ADP-ribosylagmatine, was collected for radioassay.

Figure 6:
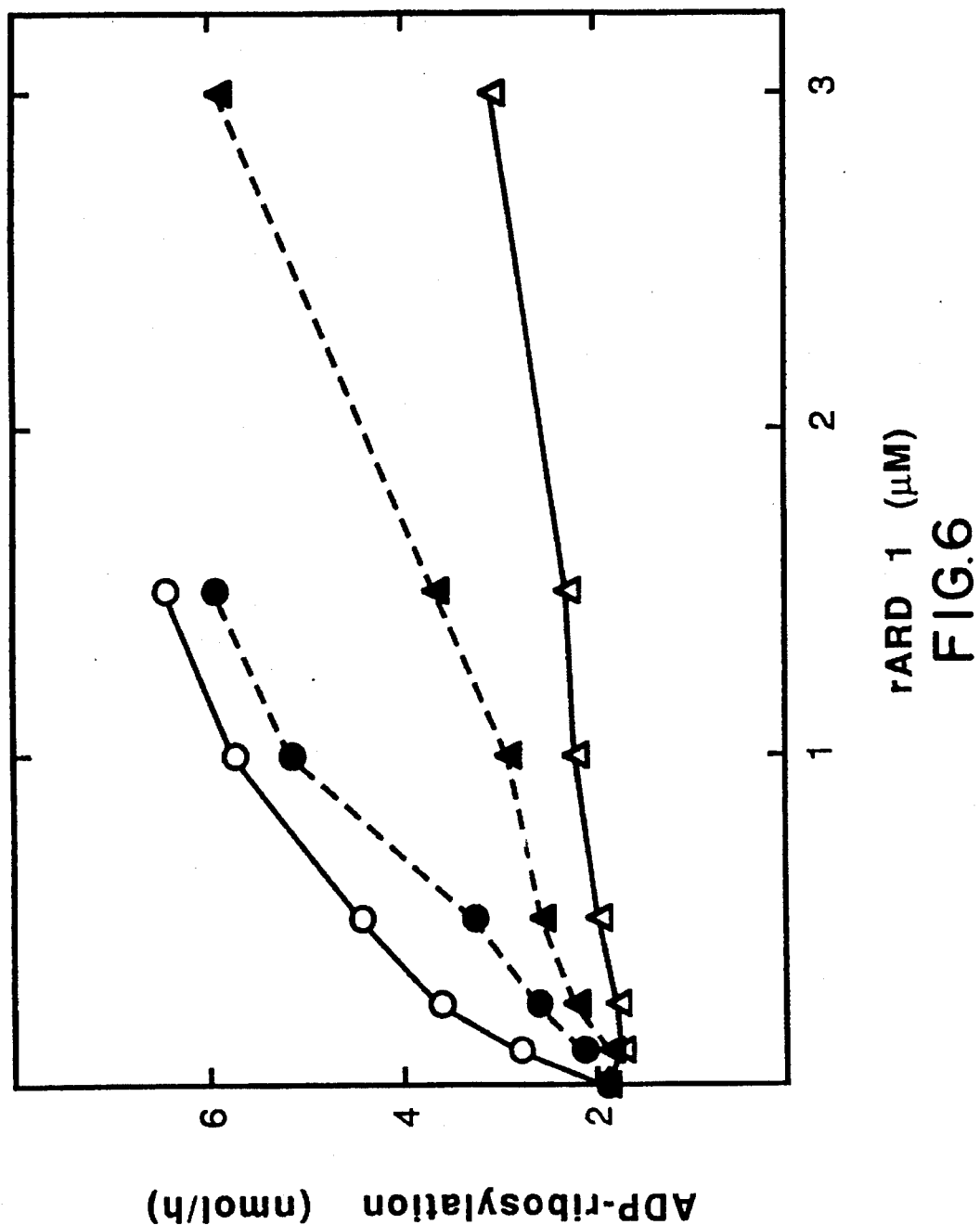
FIG. 6 is a line graph showing the effect of the increasing concentration of ARD 1 on cholera toxin-catalyzed ADP-ribosylation. Cholera toxin-catalyzed ADP-ribosylation of agmatine was assayed in the presence of indicated concentrations of recombinant ARD 1; GST-p8 (●), p8 (o), GST-p3 (▲), p3 (Δ).
Figure 7:
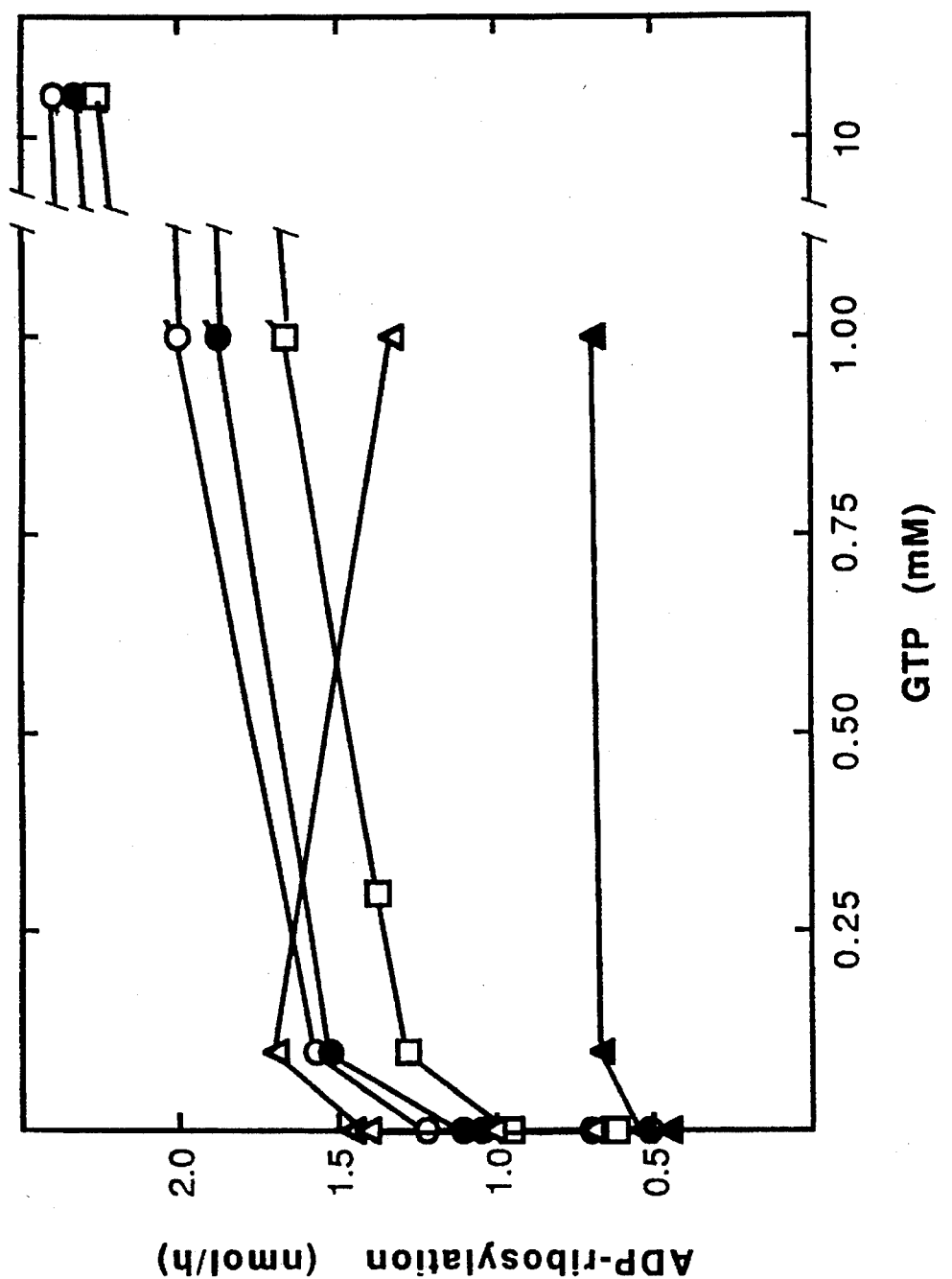
FIG. 7 is a line graph illustrating the effect of GTP concentration on ARF activity in the presence of 0.3% Tween 20. Cholera toxin-catalyzed ADP-ribosylation of agmatine with 20 µg of GST-p8 (o), 14 µg of p8 (●), 25 µg of GST-p3 (hollow box), 2 µg of sARF II (Δ) or no ARF (▲) was assayed in the presence of indicated concentration of GTP. The activities without GTP (0.1 mM GDPβS) was 0.51 nmol/h (GSTp-8), 0.64 nmol/h (p8), 0.61 nmol/h (GST-p3), 0.70 nmol/h (sARF II) and 0.46 nmol/h (no ARF).

In the presence of 0.3% Tween 20, recombinant ARD 1, p8, and GST-p8, increased the toxin ADP-ribosyltransferase in a dose-dependent manner (FIG. 6). The activity of GST-p3 was clearly less, whereas p3 had little if any activity. Maximal activation seemed to be similar; half-maximal activation was achieved with 0.5 μM p8, 0.75 μM GST-p8 and 2 μM GST-3 (FIG. 6). sARF II also stimulated the toxin transferase activity in Tween 20 (FIG. 7), although to a lesser extent than it did in the presence of SDS, DMPC/cholate, or cardiolipin (FIG. 5). GST-p5, p5, or GST did not enhance cholera toxin activity (data not shown). Activity of the recombinant ARD 1 proteins was dependent on GTP (FIG. 7), as is the case with the ARFs.

Monoclonal antibodies against ARD 1 could be useful for the reasons cited above and can be produced by the following method.

Example 8: Production of Monoclonal Antibodies

Monoclonal antibodies to ARD 1 are generated using conventional techniques, such as those disclosed in *Basic Methods in Molecular Biology* 351 (Davis, et al., 1986). Briefly, ten mice are each innoculated intraperitoneally with 500 μg of human ARD 1 antigen in a 1:1 emulsion with complete Freund's adjuvant. Thereafter, the mice are boosted with three additional injections at 15 day intervals of the same amount of antigen in a 1:1 emulsion with incomplete Freund's adjuvant. Three days following the third booster injection, the mice are sacrificed and the spleens are harvested. The spleen cells are separated and fused with myeloma cells according to the method of Kohler and Milstein by combining the spleen cells with mouse myeloma cells in a ratio of 6:1, centrifuging at 4000×g for 10 minutes, loosening the pellet with 1 ml 50% PEG, adding 9 ml DMEM, centrifuging again at 600×g for 10 minutes, and growing the cells in HAT in a 96 well tissue culture plate. Positive clones are expanded and the supernatant is screened against ARD 1.

Once antibodies against ARD 1 have been produced they can be used in asssays such as an ELISA, as discussed below.

Example 9: ELISA for Antibodies Against ARD 1

A sample from either an organism or a hybridoma is screened for the presence of ARD 1 using a conventional ELISA. Briefly, 200 μl of purified ARD 1 is added to a well of a microtiter plate and is permitted to bind to the plastic plate for 48 hours at 4° C. The well is washed with 0.15M NaCl containing 0.05% Tween 20. Sample is mixed with PBS containing 0.05% Tween 20 and BSA at 0.1 mg/ml, and aliquots are added to the treated plastic well. Plates are incubated for 1 hr at room temperature, washed, and 200 μl of 1:400 goat-antimouse IgG conjugated to alkaline phosphatase is added. After a 1 hour incubation, the well is again washed, after which 200 μl of p-nitrophenyl phosphate is added. Color development takes about one hour; development of color indicates a positive assay.

From the above data it is tempting to speculate that ARD 1 is related to a new family of larger ARF proteins and representing larger GTP-binding proteins that contain a domain with ARF structure and function as well as another domain whose function is at present unknown.

It can be appreciated that the previous experiments are only illustrative of specific embodiements of the present invention. This invention should not be limited to those embodiments disclosed by the aforementioned experiments, but only by the following claims.

What is claimed is:

1. An ARD 1 protein composition, comprising an isolated polypeptide having the amino acid sequence of SEQ ID NO:2.

2. The composition of claim 1, wherein the polypeptide is in substantially purified form.

3. An immunoassay kit, comprising:

a polypeptide reagent comprising a polypeptide having the amino acid sequence of SEQ ID NO:2;

a reaction unit including a reaction zone in which the polypeptide reagent can interact with antibodies, if any, having a binding affinity for said polypeptide to form an immunological complex; and means for detecting the reaction or lack of reaction of said polypeptide with said antibodies.

\* \* \* \* \*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 3312 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..1725

( x i ) SEQUENCE DESCRIPTION: SEQ ID NO:1:

```
ATG  GCT  ACC  CTG  GTT  GTA  AAC  AAG  CTC  GGA  GCG  GGA  GTA  GAC  AGT  GGC        48
Met  Ala  Thr  Leu  Val  Val  Asn  Lys  Leu  Gly  Ala  Gly  Val  Asp  Ser  Gly
 1              5                        10                       15

CGG  CAG  GGC  AGC  CGG  GGG  ACA  GCT  GTA  GTG  AAG  GTG  CTA  GAG  TGT  GGA        96
Arg  Gln  Gly  Ser  Arg  Gly  Thr  Ala  Val  Val  Lys  Val  Leu  Glu  Cys  Gly
            20                       25                       30

GTT  TGT  GAA  GAT  GTC  TTT  TCT  TTG  CAA  GGA  GAC  AAA  GTT  CCC  CGT  CTT       144
Val  Cys  Glu  Asp  Val  Phe  Ser  Leu  Gln  Gly  Asp  Lys  Val  Pro  Arg  Leu
        35                       40                       45

TTG  CTT  TGT  GGC  CAT  ACC  GTC  TGT  CAT  GAC  TGT  CTC  ACT  CGC  CTA  CCT       192
```

|  |  |  |  |  |  |  |  |  |  |  |  |  |  |  |  |
|---|---|---|---|---|---|---|---|---|---|---|---|---|---|---|---|
| Leu | Leu | Cys | Gly | His | Thr | Val | Cys | His | Asp | Cys | Leu | Thr | Arg | Leu | Pro |
|  | 50 |  |  |  |  | 55 |  |  |  | 60 |  |  |  |  |  |

| CTT | CAT | GGA | AGA | GCA | ATC | CGT | TGC | CCA | TTT | GAT | CGA | CAA | GTA | ACA | GAC | 240 |
|---|---|---|---|---|---|---|---|---|---|---|---|---|---|---|---|---|
| Leu | His | Gly | Arg | Ala | Ile | Arg | Cys | Pro | Phe | Asp | Arg | Gln | Val | Thr | Asp |  |
| 65 |  |  |  | 70 |  |  |  |  | 75 |  |  |  |  | 80 |  |  |

| CTA | GGT | GAT | TCA | GGT | GTC | TGG | GGA | TTG | AAA | AAA | AAT | TTT | GCT | TTA | TTG | 288 |
|---|---|---|---|---|---|---|---|---|---|---|---|---|---|---|---|---|
| Leu | Gly | Asp | Ser | Gly | Val | Trp | Gly | Leu | Lys | Lys | Asn | Phe | Ala | Leu | Leu |  |
|  |  |  |  | 85 |  |  |  |  | 90 |  |  |  |  | 95 |  |  |

| GAG | CTT | TTG | GAA | CGA | CTG | CAG | AAT | GGG | CCT | ATT | GGT | CAG | TAT | GGA | GCT | 336 |
|---|---|---|---|---|---|---|---|---|---|---|---|---|---|---|---|---|
| Glu | Leu | Leu | Glu | Arg | Leu | Gln | Asn | Gly | Pro | Ile | Gly | Gln | Tyr | Gly | Ala |  |
|  |  |  | 100 |  |  |  |  | 105 |  |  |  |  | 110 |  |  |  |

| GCA | GAA | GAA | TCC | ATT | GGG | ATA | TCT | GGA | GAG | AGC | ATC | ATT | CGT | TGT | GAT | 384 |
|---|---|---|---|---|---|---|---|---|---|---|---|---|---|---|---|---|
| Ala | Glu | Glu | Ser | Ile | Gly | Ile | Ser | Gly | Glu | Ser | Ile | Ile | Arg | Cys | Asp |  |
|  |  | 115 |  |  |  |  | 120 |  |  |  |  | 125 |  |  |  |  |

| GAA | GAT | GAA | GCT | CAC | CTT | GCC | TCT | GTA | TAT | TGC | ACT | GTG | TGT | GCA | ACT | 432 |
|---|---|---|---|---|---|---|---|---|---|---|---|---|---|---|---|---|
| Glu | Asp | Glu | Ala | His | Leu | Ala | Ser | Val | Tyr | Cys | Thr | Val | Cys | Ala | Thr |  |
|  | 130 |  |  |  |  | 135 |  |  |  |  | 140 |  |  |  |  |  |

| CAT | TTG | TGC | TCT | GAG | TGT | TCT | CAA | GTT | ACT | CAT | TCT | ACA | AAG | ACA | TTA | 480 |
|---|---|---|---|---|---|---|---|---|---|---|---|---|---|---|---|---|
| His | Leu | Cys | Ser | Glu | Cys | Ser | Gln | Val | Thr | His | Ser | Thr | Lys | Thr | Leu |  |
| 145 |  |  |  |  | 150 |  |  |  |  | 155 |  |  |  |  | 160 |  |

| GCA | AAG | CAC | AGG | CGA | GTT | CCT | CTA | GCT | GAT | AAA | CCT | CAT | GAG | AAA | ACT | 528 |
|---|---|---|---|---|---|---|---|---|---|---|---|---|---|---|---|---|
| Ala | Lys | His | Arg | Arg | Val | Pro | Leu | Ala | Asp | Lys | Pro | His | Glu | Lys | Thr |  |
|  |  |  |  | 165 |  |  |  |  | 170 |  |  |  |  | 175 |  |  |

| ATG | TGC | TCT | CAG | CAC | CAG | GTG | CAT | GCC | ATT | GAG | TTT | GTT | TGC | TTG | GAA | 576 |
|---|---|---|---|---|---|---|---|---|---|---|---|---|---|---|---|---|
| Met | Cys | Ser | Gln | His | Gln | Val | His | Ala | Ile | Glu | Phe | Val | Cys | Leu | Glu |  |
|  |  |  | 180 |  |  |  |  | 185 |  |  |  |  | 190 |  |  |  |

| GAA | GGT | TGT | CAA | ACT | AGC | CCA | CTC | ATG | TGC | TGT | GTC | TGC | AAA | GAA | TAT | 624 |
|---|---|---|---|---|---|---|---|---|---|---|---|---|---|---|---|---|
| Glu | Gly | Cys | Gln | Thr | Ser | Pro | Leu | Met | Cys | Cys | Val | Cys | Lys | Glu | Tyr |  |
|  |  | 195 |  |  |  |  | 200 |  |  |  |  | 205 |  |  |  |  |

| GGA | AAA | CAC | CAG | GGT | CAC | AAG | CAT | TCA | GTA | TTG | GAA | CCA | GAA | GCT | AAT | 672 |
|---|---|---|---|---|---|---|---|---|---|---|---|---|---|---|---|---|
| Gly | Lys | His | Gln | Gly | His | Lys | His | Ser | Val | Leu | Glu | Pro | Glu | Ala | Asn |  |
|  | 210 |  |  |  |  | 215 |  |  |  |  | 220 |  |  |  |  |  |

| CAG | ATC | CGA | GCA | TCA | ATT | TTA | GAT | ATG | GCT | CAC | TGC | ATA | CGG | ACC | TTC | 720 |
|---|---|---|---|---|---|---|---|---|---|---|---|---|---|---|---|---|
| Gln | Ile | Arg | Ala | Ser | Ile | Leu | Asp | Met | Ala | His | Cys | Ile | Arg | Thr | Phe |  |
| 225 |  |  |  |  | 230 |  |  |  |  | 235 |  |  |  |  | 240 |  |

| ACA | GAG | GAA | ATC | TCA | GAT | TAT | TCC | AGA | AAA | TTA | GTT | GGA | ATT | GTG | CAG | 768 |
|---|---|---|---|---|---|---|---|---|---|---|---|---|---|---|---|---|
| Thr | Glu | Glu | Ile | Ser | Asp | Tyr | Ser | Arg | Lys | Leu | Val | Gly | Ile | Val | Gln |  |
|  |  |  |  | 245 |  |  |  |  | 250 |  |  |  |  | 255 |  |  |

| CAC | ATT | GAA | GGA | GGA | GAA | CAA | ATC | GTG | GAA | GAT | GGA | ATT | GGA | ATG | GCT | 816 |
|---|---|---|---|---|---|---|---|---|---|---|---|---|---|---|---|---|
| His | Ile | Glu | Gly | Gly | Glu | Gln | Ile | Val | Glu | Asp | Gly | Ile | Gly | Met | Ala |  |
|  |  |  | 260 |  |  |  |  | 265 |  |  |  |  | 270 |  |  |  |

| CAC | ACA | GAA | CAT | GTA | CCA | GGG | ACT | GCA | GAG | AAT | GCC | CGG | TCA | TGT | ATT | 864 |
|---|---|---|---|---|---|---|---|---|---|---|---|---|---|---|---|---|
| His | Thr | Glu | His | Val | Pro | Gly | Thr | Ala | Glu | Asn | Ala | Arg | Ser | Cys | Ile |  |
|  |  | 275 |  |  |  |  | 280 |  |  |  |  | 285 |  |  |  |  |

| CGA | GCT | TAT | TTT | TAT | GAT | CTA | CAT | GAA | ACT | CTG | TGT | CGT | CAA | GAA | GAA | 912 |
|---|---|---|---|---|---|---|---|---|---|---|---|---|---|---|---|---|
| Arg | Ala | Tyr | Phe | Tyr | Asp | Leu | His | Glu | Thr | Leu | Cys | Arg | Gln | Glu | Glu |  |
|  | 290 |  |  |  |  | 295 |  |  |  |  | 300 |  |  |  |  |  |

| ATG | GCT | CTA | AGT | GTT | GTT | GAT | GCT | CAT | GTT | CGT | GAA | AAA | TTG | ATT | TGG | 960 |
|---|---|---|---|---|---|---|---|---|---|---|---|---|---|---|---|---|
| Met | Ala | Leu | Ser | Val | Val | Asp | Ala | His | Val | Arg | Glu | Lys | Leu | Ile | Trp |  |
| 305 |  |  |  |  | 310 |  |  |  |  | 315 |  |  |  |  | 320 |  |

| CTC | AGG | CAG | CAA | CAA | GAA | GAT | ATG | ACT | ATT | TTG | TTG | TCA | GAG | GTT | TCT | 1008 |
|---|---|---|---|---|---|---|---|---|---|---|---|---|---|---|---|---|
| Leu | Arg | Gln | Gln | Gln | Glu | Asp | Met | Thr | Ile | Leu | Leu | Ser | Glu | Val | Ser |  |
|  |  |  |  | 325 |  |  |  |  | 330 |  |  |  |  | 335 |  |  |

| GCA | GCC | TGC | CTC | CAC | TGT | GAA | AAG | ACT | TTG | CAG | CAG | GAT | GAT | TGT | AGA | 1056 |
|---|---|---|---|---|---|---|---|---|---|---|---|---|---|---|---|---|
| Ala | Ala | Cys | Leu | His | Cys | Glu | Lys | Thr | Leu | Gln | Gln | Asp | Asp | Cys | Arg |  |
|  |  |  | 340 |  |  |  |  | 345 |  |  |  |  | 350 |  |  |  |

| GTT | GTC | TTG | GCA | AAA | CAG | GAA | ATT | ACA | AGG | TTA | CTG | GAA | ACA | TTG | CAG | 1104 |
|---|---|---|---|---|---|---|---|---|---|---|---|---|---|---|---|---|
| Val | Val | Leu | Ala | Lys | Gln | Glu | Ile | Thr | Arg | Leu | Leu | Glu | Thr | Leu | Gln |  |
|  |  | 355 |  |  |  |  | 360 |  |  |  |  | 365 |  |  |  |  |

| AAA | CAG | CAG | CAG | CAG | TTT | ACA | GAA | GTT | GCA | GAT | CAC | ATT | CAG | TTG | GAT | 1152 |

|  |  |  |  |  |  |  |  |  |  |  |  |  |  |  |  |  |
|---|---|---|---|---|---|---|---|---|---|---|---|---|---|---|---|---|
| Lys | Gln | Gln | Gln | Gln | Phe | Thr | Glu | Val | Ala | Asp | His | Ile | Gln | Leu | Asp | |
| | 370 | | | | | 375 | | | | | 380 | | | | | |

```
GCC AGC ATC CCT GTC ACT TTT ACA AAG GAT AAT CGA GTT CAC ATT GGA       1200
Ala Ser Ile Pro Val Thr Phe Thr Lys Asp Asn Arg Val His Ile Gly
385             390                 395                 400

CCA AAA ATG GAA ATT CGG GTC GTT ACG TTA GGA TTG GAT GGT GCT GGA       1248
Pro Lys Met Glu Ile Arg Val Val Thr Leu Gly Leu Asp Gly Ala Gly
            405                 410                 415

AAA ACT ACT ATC TTG TTT AAG TTA AAA CAG GAT GAA TTC ATG CAG CCC       1296
Lys Thr Thr Ile Leu Phe Lys Leu Lys Gln Asp Glu Phe Met Gln Pro
                420                 425                 430

ATT CCA ACA ATT GGT TTT AAC GTG GAA ACT GTA GAA TAT AAA AAT CTA       1344
Ile Pro Thr Ile Gly Phe Asn Val Glu Thr Val Glu Tyr Lys Asn Leu
        435                 440                 445

AAA TTC ACT ATT TGG GAT GTA GGT GGA AAA CAC AAA TTA AGA CCA TTG       1392
Lys Phe Thr Ile Trp Asp Val Gly Gly Lys His Lys Leu Arg Pro Leu
450                 455                 460

TGG AAA CAT TAT TAC CTC AAT ACT CAA GCT GTT GTG TTT GTT GTA GAT       1440
Trp Lys His Tyr Tyr Leu Asn Thr Gln Ala Val Val Phe Val Val Asp
465                 470                 475                 480

AGC AGT CAT AGA GAC AGA ATT AGT GAA GCA CAC AGC GAA CTT GCA AAG       1488
Ser Ser His Arg Asp Arg Ile Ser Glu Ala His Ser Glu Leu Ala Lys
                485                 490                 495

TTG TTA ACG GAA AAA GAA CTC CGA GAT GCT CTG CTC CTG ATT TTT GCT       1536
Leu Leu Thr Glu Lys Glu Leu Arg Asp Ala Leu Leu Leu Ile Phe Ala
            500                 505                 510

AAC AAA CAG GAT GTT GCT GGA GCA CTG TCA GTA GAA GAA ATC ACT GAA       1584
Asn Lys Gln Asp Val Ala Gly Ala Leu Ser Val Glu Glu Ile Thr Glu
        515                 520                 525

CTA CTC AGT CTC CAT AAA TTA TGC TGT GGC CGT AGC TGG TAT ATT CAG       1632
Leu Leu Ser Leu His Lys Leu Cys Cys Gly Arg Ser Trp Tyr Ile Gln
530                 535                 540

GGC TGT GAT GCT CGA AGT GGT ATG GGA CTG TAT GAA GGG TTG GAC TGG       1680
Gly Cys Asp Ala Arg Ser Gly Met Gly Leu Tyr Glu Gly Leu Asp Trp
545                 550                 555                 560

CTC TCA CGG CAA CTT GTA GCT GCT GGA GTA TTG GAT GTT GCT TGATTTTAAA   1732
Leu Ser Arg Gln Leu Val Ala Ala Gly Val Leu Asp Val Ala
                565                 570                 575

GGCAGCAGTT GTTTGAAGTT TTGTGGTTAA AAGTAACTTT GCACATAAAA AAAAAAAAAA    1792
AAAATGCATC TCAAAGATG  GTAATTTAGG ATGCATATAT ATATATATAT ATATAAAGGA    1852
ATCTTGGATT GGGAATTCAG TACTTTGCTT TAAAAAAATT TTGTGGCAGA ATTAAATTTC    1912
TAATTGACGC AGATTAGATT GAATTAAATA GAAACTTATT GAATATACAT TCTTTTAAAA    1972
AGTATATTTG TTATTTAAGT TTTTCAGATA ATATGTGACC AATATACTGG GAAAGAGGTA    2032
GTCACAGAGA AAGGGTAAGT GAAGGTTTAT TCTTTCAGTG AAAAAGAAT  AGCCAATTGA    2092
GTGCCTAATG AGACCTCTGT GTGAAGCAAG TGAAGTATAG CTGCTTCTTT TAACCTGCCT    2152
TTTCACTGAA TGTTGGCAGC ATTAGTAGT  AGAAATGACA GTTGCTTAAT GAAATAGAAT    2212
CCAAACTACA TATTTGGATA ATAGGATTAC TTTATGTTTA TGTTCAGAGT TAACAGAACA    2272
CCTTTAATGC TAAGAACTAT AAGGTACAGA AAATTAATAC TTTATATAGT GTTTTATTAA    2332
CTTTCTCCTA CAGCATTTTG TATAAAACAC AATGAGGGAG TGAAATGTTA CCCAATTAGG    2392
CTTGTCAGGT TAGTAATAAA CTGAACAGTA ATAAAACTGT GGAAGTAATT GGATCTGAAT    2452
TTATGAAAGA CCCATTTCCA GGACTGAACC TAGGTCAGAG CTCTAAATTG GTCCTTCTAT    2512
TTTTCAACAA ATTTAAAGTA ATATTTCTTT CTAATATAAT ATTGCATCCT TTGTGGGAAT    2572
GACTATAGGT AAAATGTAGT AAGTAACGCA GAACCAGGGT TGGCTTATT  TAAAAGCTAG    2632
```

| | | | | | |
|---|---|---|---|---|---|
| TGACCTAAAT | AGAAAGCGAA | CTTCAAGAGA | AGTTGTAAGT | ACAGTGGCAA | ATGCTTATTA | 2692
| CTTACTTCAA | ACTGTTTCCC | AAAATAAGTG | CATTTATTTT | GACAATAAAA | CTTAAGGCTG | 2752
| TTCATGAGAA | GGCCTTGAAA | AGTTACTCTA | GAGGAAAAAT | GTCTAAAGAA | AAAAAAAATT | 2812
| CAAAAAGTTT | ACATTAATTA | TTCAGTGTTG | TGAGTAAATA | AAAATGTGTG | CTCTTTACTG | 2872
| TTTTTCATTT | TTAAAGAATA | TTATTATGGA | AGCACGATTT | ATTTAAATAG | GTACATTGAG | 2932
| ACTTTTTTTT | TTAATGTTCT | GATACATTAG | GATGAAGTTA | AATCTTAAAT | CTTATTAGTT | 2992
| GAATTGTTGT | AAGGACAGTG | ATGTCTGGTA | ACAAGATGTG | ACTTTTGGT | AGCACTGTTG | 3052
| TGGTTCATTC | TTTTCAAATC | TATTTTTGTT | TAAAAACAAT | ACAAGTTTTA | GAAAACAAAG | 3112
| CATTAAAAAA | AAAGCCTATC | AGTATTATGG | GCAATATGTA | AATAAATAAA | TGTAATATTT | 3172
| CATCCTTTAT | TTTTCAGGTA | AAAGGTCATG | CTGTTACAGG | TGTAGTTTGT | GTGCATAAAT | 3232
| AATACTTCCG | AATTAAATTA | TTTAATATTT | GACTGATTTC | AATAACTGTG | AAAATAAAAA | 3292
| GGTGTTGTAT | TGCTTGTGAG | | | | | 3312

(2) INFORMATION FOR SEQ ID NO:2:

(i) SEQUENCE CHARACTERISTICS:
(A) LENGTH: 574 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Thr Leu Val Val Asn Lys Leu Gly Ala Gly Val Asp Ser Gly
 1               5                  10                  15

Arg Gln Gly Ser Arg Gly Thr Ala Val Val Lys Val Leu Glu Cys Gly
             20                  25                  30

Val Cys Glu Asp Val Phe Ser Leu Gln Gly Asp Lys Val Pro Arg Leu
         35                  40                  45

Leu Leu Cys Gly His Thr Val Cys His Asp Cys Leu Thr Arg Leu Pro
     50                  55                  60

Leu His Gly Arg Ala Ile Arg Cys Pro Phe Asp Arg Gln Val Thr Asp
 65                  70                  75                  80

Leu Gly Asp Ser Gly Val Trp Gly Leu Lys Lys Asn Phe Ala Leu Leu
                 85                  90                  95

Glu Leu Leu Glu Arg Leu Gln Asn Gly Pro Ile Gly Gln Tyr Gly Ala
            100                 105                 110

Ala Glu Glu Ser Ile Gly Ile Ser Gly Glu Ser Ile Ile Arg Cys Asp
        115                 120                 125

Glu Asp Glu Ala His Leu Ala Ser Val Tyr Cys Thr Val Cys Ala Thr
    130                 135                 140

His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Cys Val Cys Lys Glu Tyr
        195                 200                 205

Gly Lys His Gln Gly His Lys His Ser Val Leu Glu Pro Glu Ala Asn
    210                 215                 220

Gln Ile Arg Ala Ser Ile Leu Asp Met Ala His Cys Ile Arg Thr Phe
```

|  |  |  | 225 |  |  |  | 230 |  |  |  | 235 |  |  |  | 240 |
|---|---|---|---|---|---|---|---|---|---|---|---|---|---|---|---|
| Thr | Glu | Glu | Ile | Ser | Asp | Tyr | Ser | Arg | Lys | Leu | Val | Gly | Ile | Val | Gln |
|  |  |  |  | 245 |  |  |  |  | 250 |  |  |  |  | 255 |  |
| His | Ile | Glu | Gly | Gly | Glu | Gln | Ile | Val | Glu | Asp | Gly | Ile | Gly | Met | Ala |
|  |  |  | 260 |  |  |  | 265 |  |  |  | 270 |  |  |  |  |
| His | Thr | Glu | His | Val | Pro | Gly | Thr | Ala | Glu | Asn | Ala | Arg | Ser | Cys | Ile |
|  |  | 275 |  |  |  |  | 280 |  |  |  |  | 285 |  |  |  |
| Arg | Ala | Tyr | Phe | Tyr | Asp | Leu | His | Glu | Thr | Leu | Cys | Arg | Gln | Glu | Glu |
|  | 290 |  |  |  |  | 295 |  |  |  |  | 300 |  |  |  |  |
| Met | Ala | Leu | Ser | Val | Val | Asp | Ala | His | Val | Arg | Glu | Lys | Leu | Ile | Trp |
| 305 |  |  |  |  | 310 |  |  |  |  | 315 |  |  |  |  | 320 |
| Leu | Arg | Gln | Gln | Gln | Glu | Asp | Met | Thr | Ile | Leu | Leu | Ser | Glu | Val | Ser |
|  |  |  |  | 325 |  |  |  |  | 330 |  |  |  |  | 335 |  |
| Ala | Ala | Cys | Leu | His | Cys | Glu | Lys | Thr | Leu | Gln | Gln | Asp | Asp | Cys | Arg |
|  |  |  | 340 |  |  |  |  | 345 |  |  |  |  | 350 |  |  |
| Val | Val | Leu | Ala | Lys | Gln | Glu | Ile | Thr | Arg | Leu | Leu | Glu | Thr | Leu | Gln |
|  |  |  | 355 |  |  |  |  | 360 |  |  |  |  | 365 |  |  |
| Lys | Gln | Gln | Gln | Gln | Phe | Thr | Glu | Val | Ala | Asp | His | Ile | Gln | Leu | Asp |
|  | 370 |  |  |  |  |  | 375 |  |  |  |  | 380 |  |  |  |
| Ala | Ser | Ile | Pro | Val | Thr | Phe | Thr | Lys | Asp | Asn | Arg | Val | His | Ile | Gly |
| 385 |  |  |  |  | 390 |  |  |  |  | 395 |  |  |  |  | 400 |
| Pro | Lys | Met | Glu | Ile | Arg | Val | Val | Thr | Leu | Gly | Leu | Asp | Gly | Ala | Gly |
|  |  |  |  | 405 |  |  |  |  | 410 |  |  |  |  | 415 |  |
| Lys | Thr | Thr | Ile | Leu | Phe | Lys | Leu | Lys | Gln | Asp | Glu | Phe | Met | Gln | Pro |
|  |  |  | 420 |  |  |  |  | 425 |  |  |  |  | 430 |  |  |
| Ile | Pro | Thr | Ile | Gly | Phe | Asn | Val | Glu | Thr | Val | Glu | Tyr | Lys | Asn | Leu |
|  |  | 435 |  |  |  |  | 440 |  |  |  |  | 445 |  |  |  |
| Lys | Phe | Thr | Ile | Trp | Asp | Val | Gly | Gly | Lys | His | Lys | Leu | Arg | Pro | Leu |
|  | 450 |  |  |  |  | 455 |  |  |  |  | 460 |  |  |  |  |
| Trp | Lys | His | Tyr | Tyr | Leu | Asn | Thr | Gln | Ala | Val | Val | Phe | Val | Val | Asp |
| 465 |  |  |  |  | 470 |  |  |  |  | 475 |  |  |  |  | 480 |
| Ser | Ser | His | Arg | Asp | Arg | Ile | Ser | Glu | Ala | His | Ser | Glu | Leu | Ala | Lys |
|  |  |  |  | 485 |  |  |  |  | 490 |  |  |  |  | 495 |  |
| Leu | Leu | Thr | Glu | Lys | Glu | Leu | Arg | Asp | Ala | Leu | Leu | Leu | Ile | Phe | Ala |
|  |  |  | 500 |  |  |  |  | 505 |  |  |  |  | 510 |  |  |
| Asn | Lys | Gln | Asp | Val | Ala | Gly | Ala | Leu | Ser | Val | Glu | Glu | Ile | Thr | Glu |
|  |  | 515 |  |  |  |  | 520 |  |  |  |  | 525 |  |  |  |
| Leu | Leu | Ser | Leu | His | Lys | Leu | Cys | Cys | Gly | Arg | Ser | Trp | Tyr | Ile | Gln |
|  | 530 |  |  |  |  | 535 |  |  |  |  | 540 |  |  |  |  |
| Gly | Cys | Asp | Ala | Arg | Ser | Gly | Met | Gly | Leu | Tyr | Glu | Gly | Leu | Asp | Trp |
| 545 |  |  |  |  | 550 |  |  |  |  | 555 |  |  |  |  | 560 |
| Leu | Ser | Arg | Gln | Leu | Val | Ala | Ala | Gly | Val | Leu | Asp | Val | Ala |  |  |
|  |  |  |  | 565 |  |  |  |  | 570 |  |  |  |  |  |  |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

AATGGGCTGC ATGAATTCAT CCTGTTTTAA 30

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CCTCCTTCAA TGTGCTGCAC AATTCC 26

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TGAGTAACTT GAGAACACTC 20

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

TGCCCTGCCG GCCACTGTCT ACTCCCGCTC CGAGCTTGTT TA 42

( 2 ) INFORMATION FOR SEQ ID NO:7:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GACTAGTTCT AGATCGCGAG CGGCCGCCCT TCACCTAGGT CTGTTACTTG TCG 53

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

GGCCTGGTTC CGCGGATGGC TACCCTGGTT GTA    33

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GGCCTGGTTC CGCGGATGGA AATTCGGGTC    30

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CTGCGCCTCG CTCCTCAAGC AACATCCAA    29

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CTGCGCCTCG CTCCTTTTGG TCCAATGTG    29

( 2 ) INFORMATION FOR SEQ ID NO:12:

( i ) SEQUENCE CHARACTERISTICS:

(A) LENGTH: 14 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

ATGGGCCTCA CCAT 14

(2) INFORMATION FOR SEQ ID NO:13:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

TCTCACTGAT GGCCATAGCA 20

(2) INFORMATION FOR SEQ ID NO:14:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

TCATTTGACA GCCA 14

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

TTGATAGAAT TGGTCTAGGC TTGTTACAAC 30

(2) INFORMATION FOR SEQ ID NO:16:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO ( i v ) ANTI-SENSE: NO ( x i ) SEQUENCE DESCRIPTION: SEQ ID NO:16:

GTTGTAACAA GCCTAGACCA ATTCTATCAA                30

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GGCTAAACAG CAACATTGTT CTTGGTAAAC AATAATTGGC AACAAAAC                48

( 2 ) INFORMATION FOR SEQ ID NO:18:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

TCAGTGAGTT CCAAGGGGGT AACTTTAAAA CATTATTGGT GTGGGCTC                48

( 2 ) INFORMATION FOR SEQ ID NO:19:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

TGGAATCGGA ACTTCCAGAT CCTCATCGTC CGAGTCCGAT TCACTCTG                48

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

CTCGTGGACG ATGTTGCTGT CGACCCACGC GTCCGT                36

( 2 ) INFORMATION FOR SEQ ID NO:21:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

CTCGTGGACG ATGTTGCTGT CGACCCACGC GTCCG                 35

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

TTTGTACAAG ATCGTCGTTT TGCCAGCTGC ATCTAAGCC             39

( 2 ) INFORMATION FOR SEQ ID NO:23:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

GACTAGTTCT AGATCGCGAG CGGCCGCCAC CACCGCTATG GGC        43

( 2 ) INFORMATION FOR SEQ ID NO:24:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

CTCGTGGACG ATGTGCTGGT CGACAGCTGC CCAAACCGTC TCAG       44

(2) INFORMATION FOR SEQ ID NO:25:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

CTCGTGGACG ATGTGCTGGT CGACGTTAAC ACTCAAAACA GATTT    45

(2) INFORMATION FOR SEQ ID NO:26:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

CTCGTGGACG ATGTGCTGGT CGACTCGAAA AATCATTTTA TTAGGAATAA TTCCA    55

(2) INFORMATION FOR SEQ ID NO:27:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:27:

```
Met Gly Asn Ile Phe Ala Asn Leu Phe Lys Gly Leu Phe Gly Lys Lys
  1               5                  10                  15

Glu Met Arg Ile Leu Met Val Gly Leu Asp Ala Ala Gly Lys Thr Thr
             20                  25                  30

Ile Leu Tyr Lys Leu Lys Leu Gly Glu Ile Val Thr Thr Ile Pro Thr
         35                  40                  45

Ile Gly Phe Asn Val Glu Thr Val Glu Tyr Lys Asn Ile Ser Phe Thr
     50                  55                  60

Val Trp Asp Val Gly Gly Gln Asp Lys Ile Arg Pro Leu Trp Arg His
 65                  70                  75                  80

Tyr Phe Gln Asn Thr Gln Gly Leu Ile Phe Val Val Asp Ser Asn Asp
                 85                  90                  95

Arg Glu Arg Val Asn Glu Ala Arg Glu Glu Leu Met Arg Met Leu Ala
                100                 105                 110

Glu Asp Glu Leu Arg Asp Ala Val Leu Leu Val Phe Ala Asn Lys Gln
             115                 120                 125
```

|  |  |  |  |  |  |  |  |  |  |  |  |  |  |  |
|--|--|--|--|--|--|--|--|--|--|--|--|--|--|--|
| Asp | Leu | Pro | Asn | Ala | Met | Asn | Ala | Ala | Glu | Ile | Thr | Asp | Lys | Leu | Gly |
|  | 130 |  |  |  | 135 |  |  |  |  | 140 |  |  |  |  |
| Leu | His | Ser | Leu | Arg | His | Arg | Asn | Trp | Tyr | Ile | Gln | Ala | Thr | Cys | Ala |
| 145 |  |  |  |  | 150 |  |  |  |  | 155 |  |  |  |  | 160 |
| Thr | Ser | Gly | Asp | Gly | Leu | Tyr | Glu | Gly | Leu | Asp | Trp | Leu | Ser | Asn | Gln |
|  |  |  |  | 165 |  |  |  |  | 170 |  |  |  |  | 175 |  |
| Leu | Arg | Asn | Gln | Lys |
|  |  |  |  | 180 |

( 2 ) INFORMATION FOR SEQ ID NO:28:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:28:

|  |  |  |  |  |  |  |  |  |  |  |  |  |  |  |  |
|--|--|--|--|--|--|--|--|--|--|--|--|--|--|--|--|
| Met | Gly | Asn | Val | Phe | Glu | Lys | Leu | Phe | Lys | Ser | Leu | Phe | Gly | Lys | Lys |
| 1 |  |  |  | 5 |  |  |  |  | 10 |  |  |  |  | 15 |  |
| Glu | Met | Arg | Ile | Leu | Met | Val | Gly | Leu | Asp | Ala | Ala | Gly | Lys | Thr | Thr |
|  |  |  | 20 |  |  |  |  | 25 |  |  |  |  | 30 |  |  |
| Ile | Leu | Tyr | Lys | Leu | Lys | Leu | Gly | Glu | Ile | Val | Thr | Thr | Ile | Pro | Thr |
|  |  | 35 |  |  |  |  | 40 |  |  |  |  | 45 |  |  |  |
| Ile | Gly | Phe | Asn | Val | Glu | Thr | Val | Glu | Tyr | Lys | Asn | Ile | Ser | Phe | Thr |
|  | 50 |  |  |  |  | 55 |  |  |  |  | 60 |  |  |  |  |
| Val | Trp | Asp | Val | Gly | Gly | Gln | Asp | Lys | Ile | Arg | Pro | Leu | Trp | Arg | His |
| 65 |  |  |  |  | 70 |  |  |  |  | 75 |  |  |  |  | 80 |
| Tyr | Phe | Gln | Asn | Thr | Gln | Gly | Leu | Ile | Phe | Val | Val | Asp | Ser | Asn | Asp |
|  |  |  |  | 85 |  |  |  |  | 90 |  |  |  |  | 95 |  |
| Arg | Glu | Arg | Val | Asn | Glu | Ala | Arg | Glu | Glu | Leu | Thr | Arg | Met | Leu | Ala |
|  |  |  | 100 |  |  |  |  | 105 |  |  |  |  | 110 |  |  |
| Glu | Asp | Glu | Leu | Arg | Asp | Ala | Val | Leu | Leu | Val | Phe | Val | Asn | Lys | Gln |
|  |  |  | 115 |  |  |  |  | 120 |  |  |  |  | 125 |  |  |
| Asp | Leu | Pro | Asn | Ala | Met | Asn | Ala | Ala | Glu | Ile | Thr | Asp | Lys | Leu | Gly |
|  | 130 |  |  |  | 135 |  |  |  |  | 140 |  |  |  |  |  |
| Leu | His | Ser | Leu | Arg | Gln | Arg | Asn | Trp | Tyr | Ile | Gln | Ala | Thr | Cys | Ala |
| 145 |  |  |  |  | 150 |  |  |  |  | 155 |  |  |  |  | 160 |
| Thr | Ser | Gly | Asp | Gly | Leu | Tyr | Glu | Gly | Leu | Asp | Trp | Leu | Ser | Asn | Gln |
|  |  |  |  | 165 |  |  |  |  | 170 |  |  |  |  | 175 |  |
| Leu | Lys | Asn | Gln | Lys |
|  |  |  |  | 180 |

( 2 ) INFORMATION FOR SEQ ID NO:29:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:29:

```
Met Gly Asn Ile Phe Gly Lys Leu Leu Lys Ser Leu Ile Gly Lys Lys
1               5                   10                  15

Glu Met Arg Ile Leu Met Val Gly Leu Asp Ala Ala Gly Lys Thr Thr
                20              25              30

Ile Leu Tyr Lys Leu Lys Leu Gly Glu Ile Val Thr Thr Ile Pro Thr
            35              40              45

Ile Gly Phe Asn Val Glu Thr Val Glu Tyr Lys Asn Ile Ser Phe Thr
        50              55              60

Val Trp Asp Val Gly Gly Gln Asp Lys Ile Arg Pro Leu Trp Arg His
65              70              75              80

Tyr Phe Gln Asn Thr Gln Gly Leu Ile Phe Val Val Asp Ser Asn Asp
                85              90              95

Arg Glu Arg Val Asn Glu Ala Arg Glu Glu Leu Met Arg Met Leu Ala
            100             105             110

Glu Asp Glu Leu Arg Asp Ala Val Leu Leu Val Phe Ala Asn Lys Gln
        115             120             125

Asp Leu Pro Asn Ala Met Asn Ala Ala Glu Ile Thr Asp Lys Leu Gly
    130             135             140

Leu His Ser Leu Arg His Arg Asn Trp Tyr Ile Gln Ala Thr Cys Ala
145             150             155             160

Thr Ser Gly Asp Gly Leu Tyr Glu Gly Leu Asp Trp Leu Ala Asn Gln
                165             170             175

Leu Lys Asn Lys Lys
                180
```

( 2 ) INFORMATION FOR SEQ ID NO:30:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:30:

```
Met Gly Leu Thr Ile Ser Ser Leu Phe Ser Arg Leu Phe Gly Lys Lys
1               5                   10                  15

Gln Met Arg Ile Leu Met Val Gly Leu Asp Ala Ala Gly Lys Thr Thr
                20              25              30

Ile Leu Tyr Lys Leu Lys Leu Gly Glu Ile Val Thr Thr Ile Pro Thr
            35              40              45

Ile Gly Phe Asn Val Glu Thr Val Glu Tyr Lys Asn Ile Cys Phe Thr
        50              55              60

Val Trp Asp Val Gly Gly Gln Asp Arg Ile Arg Pro Leu Trp Lys His
65              70              75              80

Tyr Phe Gln Asn Thr Gln Gly Leu Ile Phe Val Val Asp Ser Asn Asp
                85              90              95

Arg Glu Arg Ile Gln Glu Val Ala Asp Glu Leu Gln Lys Met Leu Leu
```

|   |   |   |   |   | 100 |   |   |   |   | 105 |   |   |   |   | 110 |   |   |   |   |
|---|---|---|---|---|---|---|---|---|---|---|---|---|---|---|---|---|---|---|---|

Val Asp Glu Leu Arg Asp Ala Val Leu Leu Phe Ala Asn Lys Gln
115                 120             125

Asp Leu Pro Asn Ala Met Ala Ile Ser Glu Met Thr Asp Lys Leu Gly
130                 135             140

Leu Gln Ser Leu Arg Asn Arg Thr Trp Tyr Val Gln Ala Thr Cys Ala
145                 150             155                 160

Thr Gln Gly Thr Gly Leu Tyr Glu Gly Leu Asp Trp Leu Ser Asn Glu
                165             170                 175

Leu Ser Lys Arg
            180

( 2 ) INFORMATION FOR SEQ ID NO:31:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:31:

Met Gly Leu Thr Val Ser Ala Leu Phe Ser Arg Ile Phe Gly Lys Lys
1               5                   10                  15

Gln Met Arg Ile Leu Met Val Gly Leu Asp Ala Ala Gly Lys Thr Thr
                20                  25                  30

Ile Leu Tyr Lys Leu Lys Leu Gly Glu Ile Val Thr Thr Ile Pro Thr
            35              40                  45

Ile Gly Phe Asn Val Glu Thr Val Glu Tyr Lys Asn Ile Cys Phe Thr
        50                  55                  60

Val Trp Asp Val Gly Gly Gln Asp Lys Ile Arg Pro Leu Trp Arg His
65                  70                  75                  80

Tyr Phe Gln Asn Thr Gln Gly Leu Ile Phe Val Val Asp Ser Asn Asp
                85                  90                  95

Arg Glu Arg Val Gln Glu Ser Ala Asp Glu Leu Gln Lys Met Leu Gln
                100             105                 110

Glu Asp Glu Leu Arg Asp Ala Val Leu Leu Val Phe Ala Asn Lys Gln
            115                 120             125

Asp Met Pro Asn Ala Met Pro Val Ser Glu Leu Thr Asp Lys Leu Gly
        130                 135             140

Leu Gln His Leu Arg Ser Arg Arg Trp Tyr Val Gln Ala Thr Cys Ala
145                 150             155                 160

Thr Gln Gly Thr Gly Leu Tyr Asp Gly Leu Asp Trp Leu Ser His Glu
                165             170                 175

Leu Ser Lys Arg
            180

( 2 ) INFORMATION FOR SEQ ID NO:32:

( i ) SEQUENCE CHARACTERISTICS:
        ( A ) LENGTH: 179 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:32:

| Met | Gly | Lys | Val | Leu | Ser | Lys | Leu | Phe | Lys | Gly | Ile | Phe | Gly | Asn | Lys |
|---|---|---|---|---|---|---|---|---|---|---|---|---|---|---|---|
| 1 | | | | 5 | | | | | 10 | | | | | 15 | |
| Glu | Met | Arg | Ile | Leu | Met | Leu | Gly | Leu | Asp | Ala | Ala | Gly | Lys | Thr | Thr |
| | | | 20 | | | | | 25 | | | | | 30 | | |
| Ile | Leu | Tyr | Lys | Leu | Lys | Leu | Gly | Gln | Ser | Val | Thr | Thr | Ile | Pro | Thr |
| | | 35 | | | | | 40 | | | | | 45 | | | |
| Val | Gly | Phe | Asn | Val | Glu | Thr | Val | Thr | Tyr | Lys | Asn | Val | Lys | Phe | Asn |
| | 50 | | | | | 55 | | | | | 60 | | | | |
| Val | Trp | Asp | Val | Gly | Gly | Gln | Asp | Lys | Ile | Arg | Pro | Leu | Trp | Arg | His |
| 65 | | | | | 70 | | | | | 75 | | | | | 80 |
| Tyr | Tyr | Thr | Gly | Thr | Gln | Gly | Leu | Ile | Phe | Val | Val | Asp | Cys | Ala | Asp |
| | | | | 85 | | | | | 90 | | | | | 95 | |
| Arg | Asp | Arg | Ile | Asp | Glu | Ala | Arg | Gln | Glu | Leu | His | Arg | Ile | Ile | Asn |
| | | | 100 | | | | | 105 | | | | | 110 | | |
| Asp | Arg | Glu | Met | Arg | Asp | Ala | Ile | Ile | Leu | Ile | Phe | Ala | Asn | Lys | Gln |
| | | 115 | | | | | 120 | | | | | 125 | | | |
| Asp | Leu | Pro | Asp | Ala | Met | Lys | Pro | His | Glu | Ile | Gln | Glu | Lys | Leu | Gly |
| | 130 | | | | | 135 | | | | | 140 | | | | |
| Leu | Thr | Arg | Ile | Arg | Asp | Arg | Asn | Trp | Tyr | Val | Gln | Pro | Ser | Cys | Ala |
| 145 | | | | | 150 | | | | | 155 | | | | | 160 |
| Thr | Ser | Gly | Asp | Gly | Leu | Tyr | Glu | Gly | Leu | Thr | Trp | Leu | Thr | Ser | Asn |
| | | | | 165 | | | | | 170 | | | | | 175 | |
| Tyr | Lys | Ser | | | | | | | | | | | | | |

( 2 ) INFORMATION FOR SEQ ID NO:33:

( i ) SEQUENCE CHARACTERISTICS:
( A ) LENGTH: 187 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:33:

| Met | Gly | Asn | Ile | Phe | Ala | Asn | Leu | Phe | Lys | Gly | Leu | Phe | Gly | Lys | Lys |
|---|---|---|---|---|---|---|---|---|---|---|---|---|---|---|---|
| 1 | | | | 5 | | | | | 10 | | | | | 15 | |
| Glu | Ile | Arg | Val | Val | Thr | Leu | Gly | Leu | Asp | Gly | Ala | Gly | Lys | Thr | Thr |
| | | | 20 | | | | | 25 | | | | | 30 | | |
| Ile | Phe | Tyr | Lys | Leu | Gln | Asp | Gly | Glu | Phe | Met | Gln | Pro | Ile | Pro | Thr |
| | | 35 | | | | | 40 | | | | | 45 | | | |
| Ile | Gly | Phe | Asn | Val | Glu | Thr | Val | Glu | Tyr | Lys | Asn | Leu | Lys | Phe | Thr |
| | | | 50 | | | | 55 | | | | | 60 | | | |
| Ile | Trp | Asp | Val | Gly | Gly | Lys | His | Lys | Leu | Arg | Pro | Leu | Trp | Lys | His |
| 65 | | | | | 70 | | | | | 75 | | | | | 80 |

```
Tyr Tyr Leu Asn Thr Gln Ala Val Val Phe Val Val Asp Ser Ser His
                85                  90                  95

Arg Asp Arg Ile Ser Glu Ala His Ser Glu Leu Ala Lys Leu Leu Thr
            100                 105                 110

Glu Lys Glu Leu Arg Asp Ala Leu Leu Leu Ile Phe Ala Asn Lys Gln
        115                 120                 125

Asp Val Ala Gly Ala Leu Ser Val Glu Glu Ile Thr Glu Leu Leu Ser
    130                 135                 140

Leu His Lys Leu Cys Cys Gly Arg Ser Trp Tyr Ile Gln Gly Cys Asp
145                 150                 155                 160

Ala Arg Ser Gly Met Gly Leu Tyr Glu Gly Leu Asp Trp Leu Ser Arg
                165                 170                 175

Gln Leu Val Ala Ala Gly Val Leu Asp Val Ala
                180             185
```

( 2 ) INFORMATION FOR SEQ ID NO:34:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:34:

GACTAGTTCT AGATCGCGAG CGGCCGCCCT GGATATCTAA CCAAGGACAT    50